(12) United States Patent
Tsang et al.

(10) Patent No.: US 10,434,017 B2
(45) Date of Patent: Oct. 8, 2019

(54) ELASTIC COMPOSITE HAVING CROSS-DIRECTIONAL ELASTICITY AND A SYSTEM AND METHOD FOR MAKING THE ELASTIC COMPOSITE

(71) Applicant: DSG TECHNOLOGY HOLDINGS LTD., Road Town, Tortola (VG)

(72) Inventors: Patrick King Yu Tsang, Tuen Mun (HK); Eugenio Varona, Marietta, GA (US); Andrew C. Wright, Derbyshire (GB); Anne Smid, Wolvega (NL)

(73) Assignee: DSG Technology Holdings Ltd., Kwai Chung, N.T., (HK)

( * ) Notice: Subject to any disclaimer, the term of this patent is extended or adjusted under 35 U.S.C. 154(b) by 1060 days.

(21) Appl. No.: 14/614,860

(22) Filed: Feb. 5, 2015

(65) Prior Publication Data
US 2015/0216737 A1 Aug. 6, 2015

Related U.S. Application Data

(63) Continuation of application No. 13/953,980, filed on Jul. 30, 2013, now Pat. No. 8,961,487, which is a
(Continued)

(51) Int. Cl.
*A61F 13/49* (2006.01)
*A61F 13/15* (2006.01)
(Continued)

(52) U.S. Cl.
CPC .. *A61F 13/49012* (2013.01); *A61F 13/15593* (2013.01); *A61F 13/15674* (2013.01);
(Continued)

(58) Field of Classification Search
CPC .......... A61F 13/15593; A61F 13/49012; A61F 13/49014; A61F 13/15674;
(Continued)

(56) References Cited

U.S. PATENT DOCUMENTS

| 1,195,949 A | 8/1916 | Carney |
| 2,718,254 A | 9/1955 | Carlson |
| (Continued) | | |

FOREIGN PATENT DOCUMENTS

| CN | 101146680 | 3/2008 |
| EP | 0251251 | 1/1988 |
| (Continued) | | |

OTHER PUBLICATIONS

Office Action dated Sep. 16, 2015, issued in Canadian Patent Application No. 2,745,924; 4 pages.
(Continued)

*Primary Examiner* — Vishal I Patel
(74) *Attorney, Agent, or Firm* — Alberto Q. Amatong, Jr.; Amatong McCoy LLC

(57) ABSTRACT

A method of making an elastic composite is described that entails conveying a first sheet of material on a conveyor, and wrapping a section of elastic about the first sheet and the conveyor, thereby applying elastics cross directionally across the first sheets. A second sheet of material is applied onto the first sheet having elastics applied thereon, thereby creating a subcomposite including the first sheet, the second sheet, and elastics sandwiched therebetween, wherein a plurality of elastics extend outward from the one side of the subcomposite, about the conveyor, and return into an opposite side of the subcomposite. The sub-composite is cut through the first and second sheets and the elastics, thereby separating the sub-composite into a first carrier and a second carrier, each carrier including a first material layer and a second material layer, whereby a plurality of spaced apart elastic elements extend from the first carrier to the second carrier, the first and second carriers defining an exposed elastic region therebetween formed by the plurality of spaced apart elastic elements.

18 Claims, 17 Drawing Sheets

Related U.S. Application Data continuation of application No. 12/386,677, filed on Apr. 20, 2009, now Pat. No. 8,529,536.

(60) Provisional application No. 61/124,697, filed on Apr. 18, 2008.

(51) Int. Cl.
| | |
|---|---|
| *B32B 37/12* | (2006.01) |
| *B32B 37/14* | (2006.01) |
| *B32B 37/18* | (2006.01) |
| *B32B 38/00* | (2006.01) |

(52) U.S. Cl.
CPC .. *A61F 13/15747* (2013.01); *A61F 13/49011* (2013.01); *A61F 13/49014* (2013.01); *B32B 37/12* (2013.01); *B32B 37/142* (2013.01); *B32B 37/18* (2013.01); *B32B 38/00* (2013.01); *B32B 2307/51* (2013.01); *B32B 2307/726* (2013.01); *B32B 2555/02* (2013.01); *Y10T 156/10* (2015.01); *Y10T 156/1044* (2015.01); *Y10T 156/1052* (2015.01); *Y10T 156/1066* (2015.01); *Y10T 156/1082* (2015.01); *Y10T 156/1084* (2015.01); *Y10T 428/24752* (2015.01); *Y10T 442/602* (2015.04)

(58) Field of Classification Search
CPC ......... A61F 13/15747; A61F 13/49011; Y10T 428/24752; Y10T 442/602; Y10T 156/10; Y10T 156/1044; Y10T 156/1084; Y10T 156/1066; Y10T 156/1082; Y10T 156/1052; B32B 2555/02; B32B 37/18; B32B 37/142; B32B 37/12; B32B 2307/726; B32B 2307/51; B32B 38/00
See application file for complete search history.

(56) References Cited

U.S. PATENT DOCUMENTS

| | | | |
|---|---|---|---|
| 2,902,395 | A | 9/1959 | Hirschy et al. |
| 3,041,230 | A | 6/1962 | Diehl |
| 3,627,621 | A | 12/1971 | Mowers |
| 3,649,411 | A | 3/1972 | Bolles |
| 3,663,331 | A | 5/1972 | Solbeck |
| 3,800,796 | A | 4/1974 | Jacob |
| 3,801,401 | A | 4/1974 | Cope et al. |
| 4,284,454 | A | 8/1981 | Joa |
| 4,527,990 | A | 7/1985 | Sigl |
| 4,602,973 | A | 7/1986 | Holroyd |
| 4,642,151 | A | 2/1987 | Coenen |
| 4,726,874 | A | 2/1988 | Vanvliet |
| 4,776,911 | A * | 10/1988 | Uda ................ A41D 27/00 156/161 |
| 4,908,089 | A | 3/1990 | Uda et al. |
| 5,004,466 | A | 4/1991 | Uda et al. |
| 5,127,981 | A | 7/1992 | Straub et al. |
| 5,221,390 | A | 6/1993 | Persson et al. |
| 5,338,382 | A | 8/1994 | Johnson et al. |
| 5,429,694 | A | 7/1995 | Herrmann |
| 5,531,729 | A | 7/1996 | Coles et al. |
| 5,531,850 | A | 7/1996 | Herrmann |
| 5,591,152 | A | 1/1997 | Buell et al. |
| 5,628,741 | A | 5/1997 | Buell et al. |
| 5,685,873 | A | 11/1997 | Bruemmer |
| 5,745,922 | A | 5/1998 | Rajala et al. |
| 5,779,691 | A | 7/1998 | Schmitt |
| 5,807,368 | A | 9/1998 | Helmer |
| 5,807,371 | A | 9/1998 | Toyoda et al. |
| 5,938,652 | A | 8/1999 | Sauer |
| 6,086,571 | A | 7/2000 | Guevara et al. |
| 6,096,151 | A | 8/2000 | Edwards |
| 6,123,694 | A | 9/2000 | Pieniak et al. |
| 6,146,369 | A | 11/2000 | Hartman et al. |
| 6,336,922 | B1 | 1/2002 | Vangompel et al. |
| 6,340,782 | B1 | 1/2002 | Kling et al. |
| 6,419,667 | B1 | 7/2002 | Avalon et al. |
| 6,425,430 | B1 | 7/2002 | Ward et al. |
| 6,454,750 | B1 | 9/2002 | Vogt et al. |
| 6,454,752 | B1 | 9/2002 | Huang et al. |
| 6,626,879 | B1 | 9/2003 | Ashton et al. |
| 6,649,001 | B2 | 11/2003 | Heden et al. |
| 6,885,112 | B2 | 2/2005 | Johnson |
| 7,361,246 | B2 | 4/2008 | Chang et al. |
| 2001/0039700 | A1 | 11/2001 | Krueger |
| 2002/0038110 | A1 | 3/2002 | Kusibojoska et al. |
| 2002/0151863 | A1 | 10/2002 | Toyoshima |
| 2002/0177829 | A1 | 11/2002 | Fell et al. |
| 2003/0064652 | A1 | 4/2003 | Heden et al. |
| 2003/0069557 | A1 | 4/2003 | Driskell et al. |
| 2003/0083634 | A1 | 5/2003 | Fernfors |
| 2003/0089454 | A1 | 5/2003 | Johnson |
| 2003/0109844 | A1 | 6/2003 | Gibbs |
| 2003/0139725 | A1 | 7/2003 | Gibbs |
| 2003/0144643 | A1 | 7/2003 | Jarpenberg et al. |
| 2004/0026011 | A1 | 2/2004 | Edwards et al. |
| 2005/0095942 | A1 | 5/2005 | Mueller et al. |
| 2005/0131373 | A1 | 6/2005 | Wright et al. |
| 2005/0139311 | A1 | 6/2005 | Chang et al. |
| 2006/0139302 | A1 | 6/2006 | Chen et al. |
| 2007/0016155 | A1 | 1/2007 | Chang et al. |
| 2007/0246152 | A1 | 10/2007 | Chang et al. |
| 2008/0093015 | A1 | 4/2008 | Chang et al. |
| 2008/0156418 | A1 | 7/2008 | Fenske |

FOREIGN PATENT DOCUMENTS

| | | |
|---|---|---|
| EP | 1188427 | 3/2002 |
| EP | 1520569 | 4/2005 |
| JP | 63-099302 | 4/1988 |
| JP | 63-243309 | 10/1988 |
| JP | 2602221 Y2 | 1/2000 |
| JP | 2002-192641 | 7/2002 |
| WO | 9519258 | 7/1995 |
| WO | 0100915 | 1/2001 |
| WO | 0232364 | 4/2002 |
| WO | 03017903 | 3/2003 |
| WO | 03041627 | 5/2003 |
| WO | 2004087416 | 10/2004 |
| WO | 2005060910 | 7/2005 |
| WO | 2005065248 | 7/2005 |
| WO | 2005115754 | 12/2005 |
| WO | 2007059933 | 5/2007 |
| WO | 2009145860 | 12/2009 |

OTHER PUBLICATIONS

International Preliminary Report on Patentability dated Oct. 6, 2011 (issued in PCT Application No. PCT/US09/02462).
Office Action dated Feb. 13, 2012, issued in Israeli Patent Application No. 170945 (Hebrew text. English translation not provided). 5 pages.
Supplementary European Search Report dated Dec. 17, 2012 (issued in EP Application No. 09755223.6) 6 pages.
Examiner's Report dated Sep. 25, 2013, issued in Australian Patent Application No. 2009251867; 4 pages.
European Supplementary Search Report dated Dec. 17, 2012, issued in EP Application No. 09755223.6; 6 pages.
Office Action dated Sep. 17, 2013, issued in CN Application No. 200980123545.9; 6 pages of Chinese Text of Office Action and 5 pages of English Text of Office Action (11 total pages).

* cited by examiner

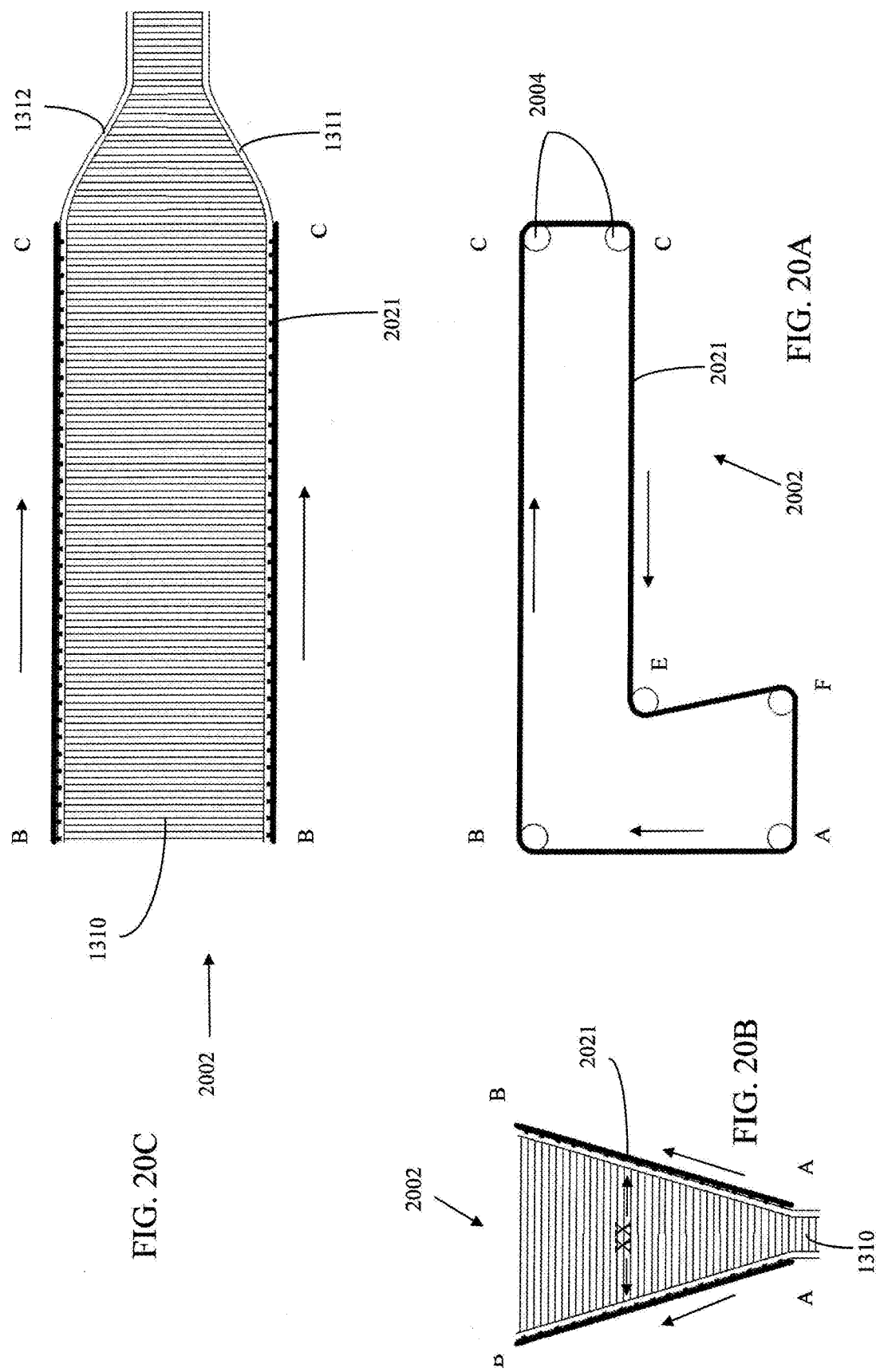

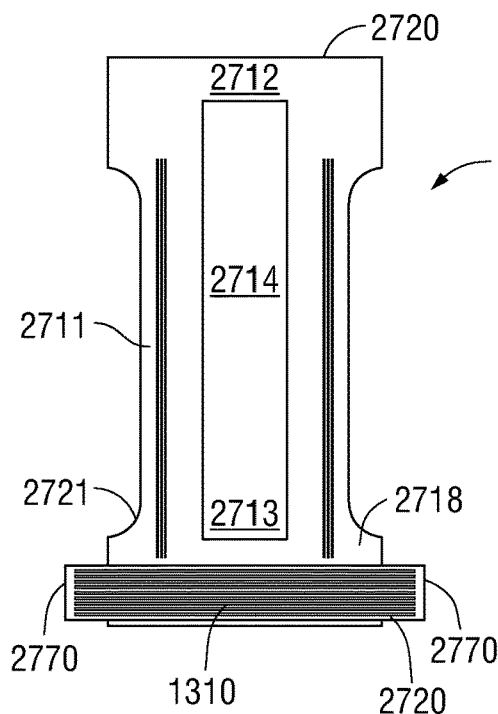
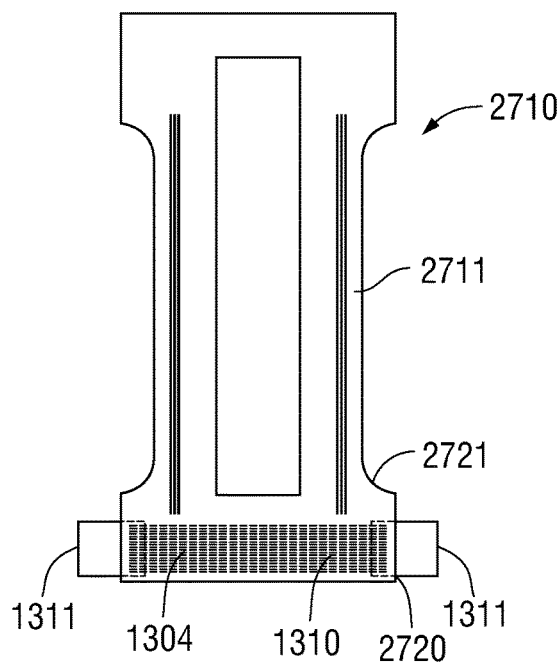
FIG. 27A    FIG. 27B
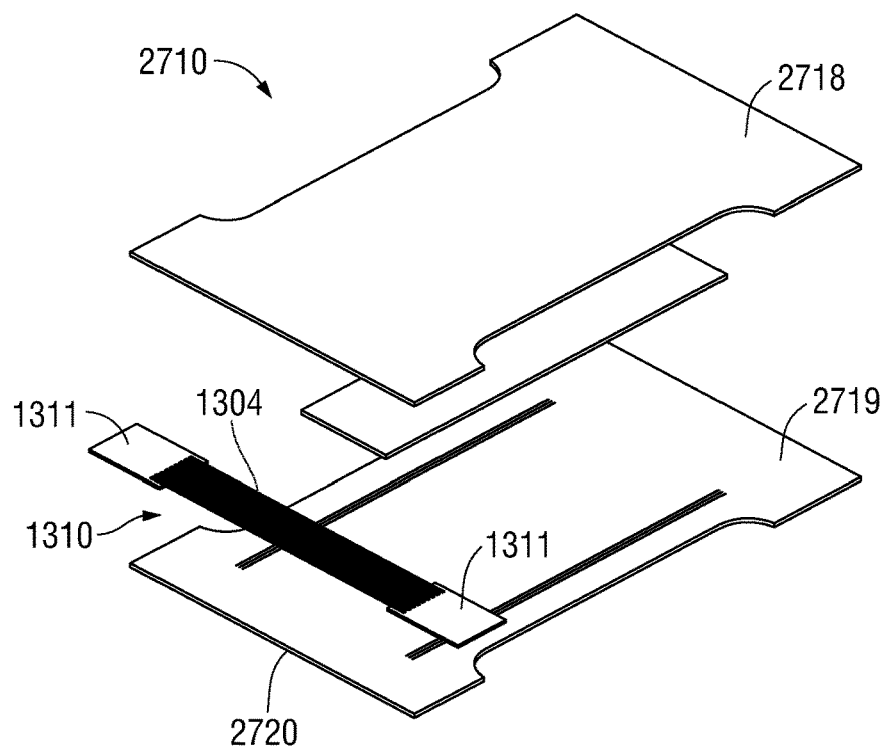
FIG. 27C

ELASTIC COMPOSITE HAVING CROSS-DIRECTIONAL ELASTICITY AND A SYSTEM AND METHOD FOR MAKING THE ELASTIC COMPOSITE

The present application is a Continuation application of U.S. application Ser. No. 13/953,980 filed on Jul. 30, 2013 (now pending), which is a Continuation application of U.S. application Ser. No. 12/386,677 filed on Apr. 20, 2009 (now U.S. Pat. No. 8,529,536 issued on Sep. 10, 2013), which claims the benefit of the filing date of U.S. Provisional Application Ser. No. 61/124,697 filed on Apr. 18, 2008 (which is hereby incorporated by reference for all purposes and made a part of the present disclosure).

BACKGROUND OF THE INVENTION

The present invention relates generally to elastic composites. More particularly, the present invention relates to an elastic composite that can be used in the manufacture of a garment, other textile or fabric structures, similar material structures, and the like, but more particularly, disposable absorbent articles and garments. The elastic composite of the present invention is well suited in providing an elastic component that can be employed in one or more areas of the disposable absorbent article. The present invention also relates to a system and method of making the elastic. The elastic composite and the system and method for making the elastic composite are particularly suited for use with or on disposable absorbent garments or articles such as baby diapers and training pants. To illustrate various aspects of the invention, exemplary and preferred embodiments are described herein in the context of disposable absorbent garments.

Disposable absorbent garments contemplated by the invention include disposable diapers, disposable pull-on garments and training pants, and the like. These garments are worn about the lower torso or waist of the user so as to receive and contain urine and other bodily wastes. The benefits provided by the use of a disposable diaper on an infant are well known and its use has become widespread. Disposable pull-on garments include training pants, pull-on diapers, disposable underwear, and adult incontinence garments. As for training pants, these garments are used by young children to facilitate a child's transition from using diapers to wearing regular underpants (i.e., during toilet training). Training pants and other disposable pull-on pants have closed sides such that the user or caregiver raises the garment about the user's legs to wear the garment and slips the garment downward about the user's legs to take it off.

The principal elements of a typical disposable absorbent garment include a liquid permeable inner layer (or topsheet), a liquid impermeable outer layer (or backsheet), and an absorbent core sandwiched between the inner and outer layers. Elastic members may be incorporated into different parts of the garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of a disposable absorbent garment. The resulting elastication allows the garment to stretch when it is put on and when it is worn. The elastication allows the garment to accommodate variations in waist size and leg size of the user, while fitting snugly about the waist and legs.

When elastic members are incorporated into a part or area of the garment, that part or area typically becomes a distinct, functional component of the garment. These elastic components include the side panels or ear portions, the waistband, and fastening tabs. The elastic components to which the present invention is directed is generally elongated, and may be a distinct portion of a larger, unitary piece, or a separate, attachable component. Furthermore, the elastic component typically contains one or more sections or layers in addition to the elastic members. In this regard, such an elastic component may be referred to as an elastic composite of the type which the present invention is concerned.

Due in part to its multi-component construction, these elastic composites may require a dedicated sub-process for manufacture which must be accommodated by the greater garment manufacturing process. Alternatively, the elastic composite may be manufactured independently or simply, manufactured in a separate sub-process detached from the central garment manufacturing system. In either case, a source of the elastic composite may be provided as input to the garment manufacturing process.

In most applications, the elastic composite has a significant impact on the fit and sealability of the garment, as well as the general appearance and construction quality of the garment. The design and construction of the elastic composite can also represent a significant portion of the cost of manufacturing the garment. It is, therefore, always desirable to provide a functionally and/or aesthetically improved elastic composite or a cost effective system and method of making the elastic composite.

It is desirable for the target elastic composite, system, and method of manufacturing to be practical, and provide functional or aesthetic attributes. It is also desirable that the design and construction of the elastic composite have a minimal, if not positive, impact on the efficiency of present systems and methods. The design and construction should also have a minimal, if not positive, impact on the overall manufacturing cost of the elastic composite or the final product.

Pending United States patent application publications US2005/0131373A1 and US/2005/0139311A1 provide background information on elastic composites (and the manufacture of such composites) of the type relevant to the present invention. Accordingly, some portions of the publications have been included herein to facilitate description of the invention. In any event, these two publications are also hereby incorporated by reference and made a part of the present disclosure, but only to the extent that incorporated subject matter provides background information and/or exemplary composites and processes suitable for use on, or with, the present inventive composites, systems, and methods. Thus, the incorporated subject matter shall not serve to limit the scope of the present invention. These pending publications and documents are also directed to an elastic composite having cross-directional elasticity, as well as a system and method of making the same. More specifically, these prior publications require elastic composites in which an elastic construction imparts generally lateral elasticity to the composite in a direction that corresponds to the cross-machine direction. Such an elastic composite provides certain advantages and benefits for the disposable absorbent article, and also, the system and method of making the elastic composite and the disposable absorbent article. For example, the provision of such an elastic composite or a sub-process of making an improved elastic composite affords flexibility, efficiency, and productivity in the system and process. These advantages and benefits translate further to cost efficiency and cost savings. Attaining these benefits and advantages presents, however, unique technical challenges. The present invention is directed, in some respects, to addressing these technical challenges.

SUMMARY OF THE INVENTION

For purposes of the present description, the term "elastic band" or "composite" refers to a multi-layer construction. In this construction, a plurality of elastic members, such as threads or strands, are connected to or disposed adjacent one or more materials, e.g., backsheet and topsheet. In this way, the elastic elements impart elasticity to the connected or adjacent layers and thus, to that part of the garment or other textile structure. Such an elastic structure may be a distinct attachable component of the garment or textile structure or may be a distinct portion or section of the garment body or textile structure or a larger, unitary component of the garment body or textile structure. As used herein, the term "elastic sub-composite" shall mean a multi-component construction combination that includes elastic elements integrated with a substrate layer. Further, an elastic sub-composite provides one component that may be integrated with other components to form the elastic composite and impart elastic properties thereto. For example, in one embodiment of the present invention, a plurality of elastics are connected with one or more carrier webs, but are substantially exposed.

In one aspect of the present invention, a method is provided for making an elastic composite having a plurality of elastics imparting cross-directional elasticity to the composite. Such an elastic composite may be referred to herein as a cross-directional elastic composite. In another aspect of the present invention, a system is provided implementing the method or for making the elastic composite. In yet another aspect of the invention, a disposable absorbent garment is provided in which such an elastic composite is attached to a central body. In yet another aspect of the invention, an elastic composite is provided having a first nonwoven layered carrier a second nonwoven layered carrier; and a plurality of mutually spaced apart, cross-directional elastic elements. The elastic elements extend generally laterally from the first carrier to the second carrier thereby forming an elastic region therebetween.

In yet another aspect of the invention, a method for making the elastic composite is provided. The method entails conveying a first sheet of material and wrapping a section of elastic about the first sheet, thereby applying elastics cross directionally across the first sheet. The method further entails applying a second sheet of material onto the first sheet having elastics applied thereon, thereby forming a subcomposite including the first sheet, the second sheet, and elastics sandwiched therebetween, wherein the elastics extend outward from one side of the subcomposite and encircle to return on an opposite side of the subcomposite. The sub-composite is then cut through the first and second sheets and the elastics to generate an elastic composite having two separated parts of the sub-composite and an exposed elastic region therebetween.

BRIEF DESCRIPTION OF THE DRAWINGS

FIG. 20A is a simplified illustration and elevation view of an alternative extender subsystem, according to the present invention;
FIG. 20B is a front elevation view of the extender subsystem;
FIG. 20C is a plan view of the extender subsystem.

FIGS. 27A, B, and C are simplified illustrations of a disposable absorbent article employing an elastic composite as a combination waist band and pair of side panels, according to the present invention.

DETAILED DESCRIPTION OF PREFERRED EMBODIMENTS OF THE INVENTION

Generally, the present invention relates to an elastic composite, and to a system and method for making the elastic composite. More particularly, the invention is directed to an elastic composite having cross-machine or cross-directional elastic or stretch properties. Such an elastic composite is sometimes referred to herein as an elastic composite having cross-directional elasticity and further, as a cross-directional elastic composite.

As described previously, various aspects of the present invention are particularly suited to or for a disposable absorbent garment, such as baby diapers and training pants. To illustrate the invention and preferred embodiments of the invention, much of the following Detailed Description will be provided in the context of such disposable absorbent garments. It is contemplated that various aspects of the inventive composite, garment, system, and process may be applicable to other material structures and processes. This Detailed Description and exemplary embodiment should not, therefore, be construed as limiting the invention to the structures, configurations, methods, and processes described herein.

FIGS. 1-10 are provided for background and to illustrate structures and processes potentially relevant to the present invention. Some Figures, and accompanying description, are provided to illustrate the prior art and for the purpose of highlighting the contributions to the prior art provided by the present invention. The same Figures also illustrate use of the elastic composite, system, or method of the invention, and/or a product derived from the inventive elastic composite.

Figure 1:
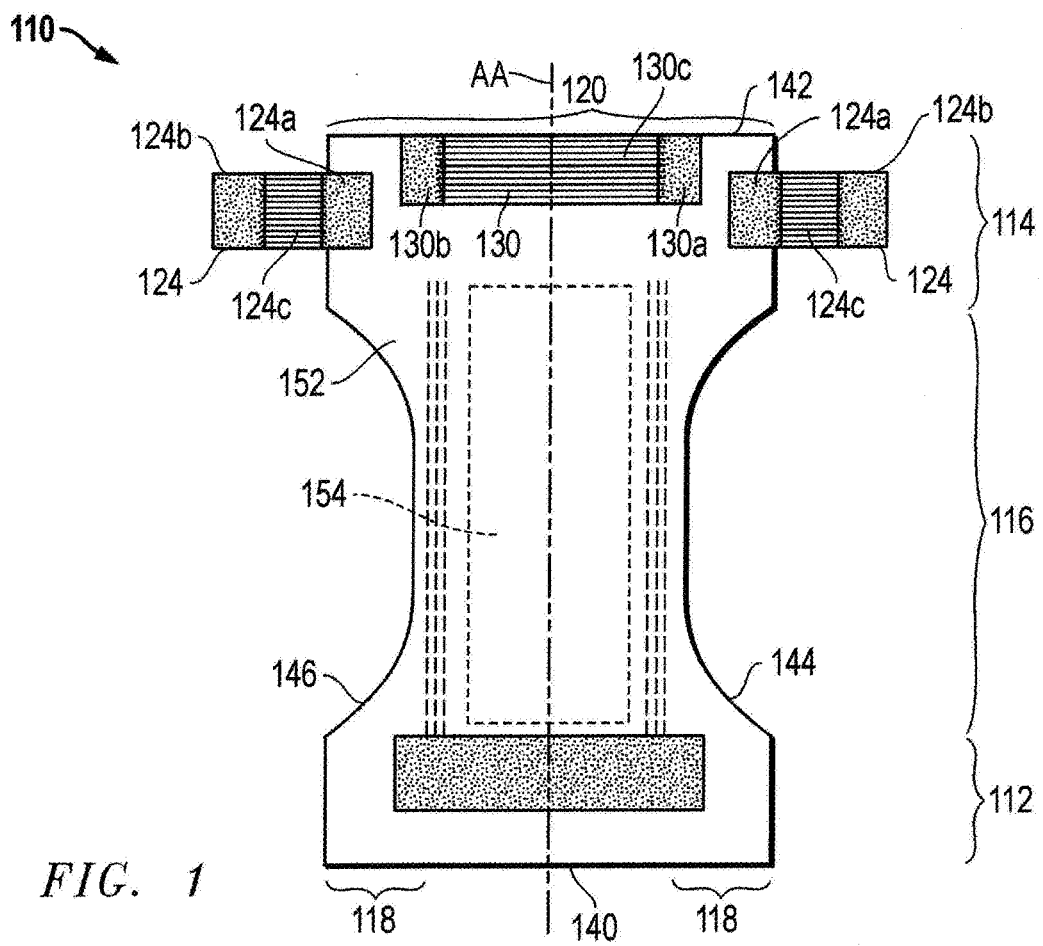
FIG. 1 is a plan view of a disposable absorbent garment in the unfolded configuration.
Figure 4:
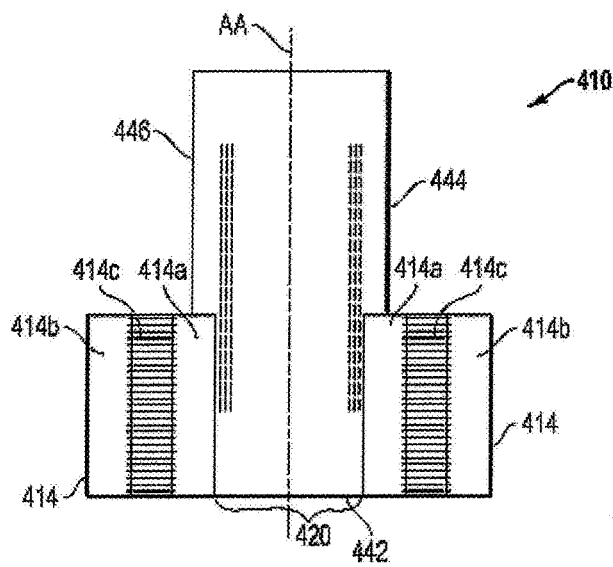
FIG. 4 is a plan view of another disposable absorbent garment.

In FIGS. 1 and 4, a disposable absorbent garment is shown that is suitable for the invention and in the form of a diaper having one or more elastic composites incorporated therein. FIGS. 6-10 illustrate a system, system components, and a process of making the elastic composite having a single elasticized region as previously described and disclosed in the prior art. See U.S. patent application Ser. Nos. 10/733,649 and 11/021,424. These Figures and accompanying descriptions of the prior art are provided to facilitate description of the present inventive elastic composite and highlight the differences and improvements provided by the present inventive system and method.

The disposable absorbent garment 110 in FIG. 1 is of a type that can be placed against or in proximity to the body of a wearer so as to absorb and to contain various bodily exudates. It should be noted, however, that the present invention is applicable to a variety of disposable absorbent articles and garments, including training pants and a variety of adult incontinence products. As will be described below, the inventive elastic composite or elastic composite band may provide a side panel or ear portion, a waistband, a fastening tab or band, or other distinct elastic component of the garment or article. The inventive elastic composite may also be incorporated into an ear portion to elasticate the ear portion or to supplement the ear portion with an elasticated fastening tab.

FIG. 1 is introduced to illustrate some basic features of a disposable diaper 110. The diaper 110 includes three main regions aligned along an imaginary longitudinal axis or plane AA. These regions include a first waist region 112 (typically at the front of the user when the garment 110 is worn), a back waist region 114, and a crotch region 116. The diaper 110 is also characterized by a front edge 140, a back longitudinal edge 142, a first lateral or side edge or side margin 144, and a second lateral or side edge or side margin 146.

Along a lateral direction, the diaper 110 includes ear regions or ear portions 118 extending laterally from the waist regions 112, 114. Together, the waist regions 112, 114 and crotch region 116 may be referred to as forming a central body portion 120 of the garment 110 that is positioned within side edges 144, 146. The body portion 120 may also be referred to as being formed by a liquid permeable inner layer or topsheet 152, a liquid impermeable outer layer or backsheet (not shown), and an absorbent core 154 sandwiched between the two layers. The ear portions 118 further include fastening tabs 124 for attaching the waist regions 112, 114 together. The diaper 110 also has an elastic waistband 130 positioned generally along the back edge 142 to facilitate fastening and to enhance the fit and seal of the diaper 110. When the hourglass shaped diaper 110 is worn, the crotch region 116 fits about the crotch of the wearer, and the front and back waist regions, 112 and 114, fit about the corresponding waist areas. The ear portions 118, on the other hand, wrap about the wearer and the fastening tabs 124 engage to form a complete, all-around waistline of the diaper 110.

Figure 2:
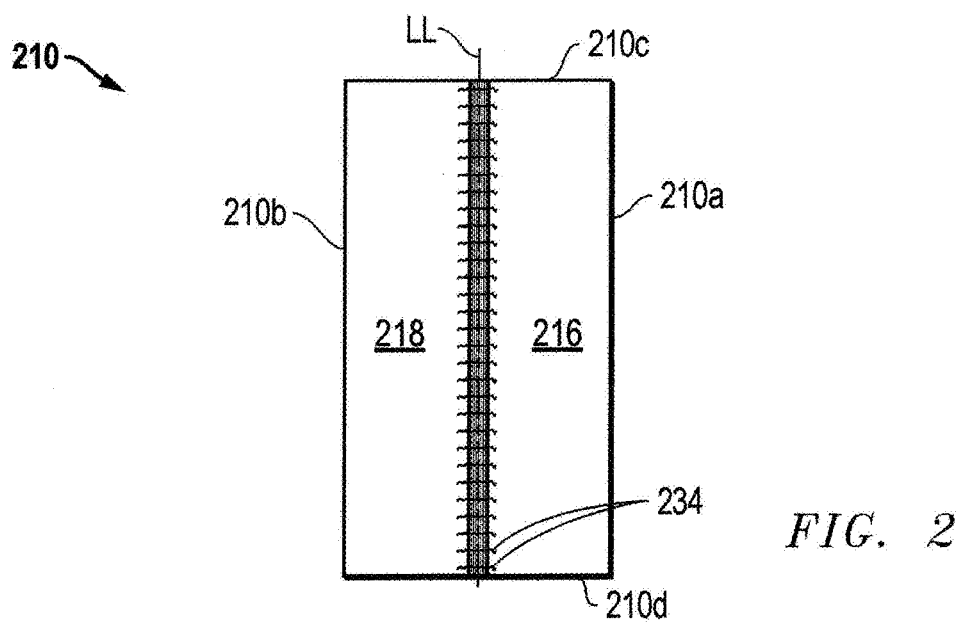
FIG. 2 is a plan view of an elastic composite of the type to which embodiments of the present invention are directed.
Figure 5:
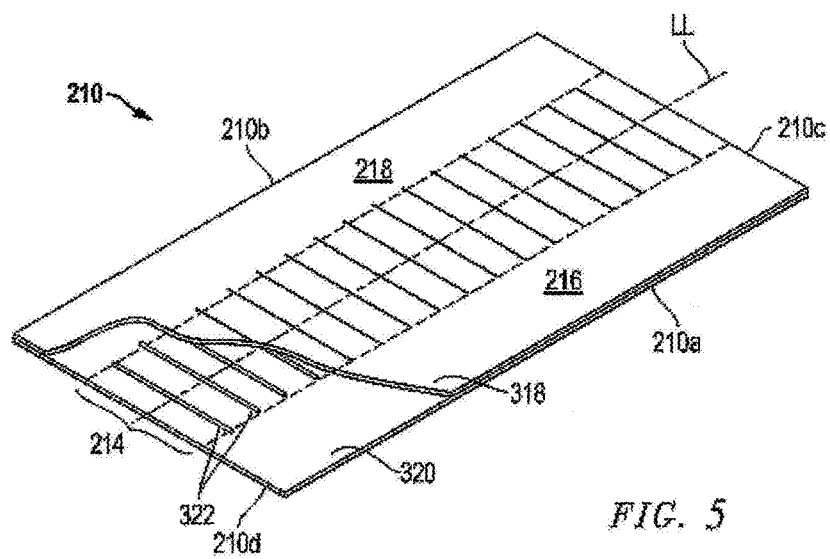
FIG. 5 is a perspective view of the elastic composite of FIG. 2 with a cut-out to show an elastic construction.

FIG. 2 depicts a typical elastic composite band 210, now generally known in the art, but which may also be derived from the elastic composite of the present invention. The elastic composite band 210 is one particularly suited for use as a side panel or fastening tab of a disposable absorbent garment (see, e.g., FIG. 1). FIG. 5 provides a perspective view and partial cutout of the elastic composite band 210. The elastic composite band 210 may be characterized by an imaginary centerline LL. The centerline LL preferably corresponds with the machine direction of the elastic composite band 210 during manufacture. The elastic band 210 also has side or longitudinally extending side edges 210a and 210b and laterally extending end edges 210c and 210d. In FIG. 2, the elastic composite band 210 is shown in the stretched state as, for example, when a garment incorporating the elastic composite band 210 is worn. In this state, the elastic composite band 210 stretches, in the lateral or cross-machine direction (denoted by arrows XX).

As used herein, the term "machine" direction refers to the direction at which the component, or more particularly, the material web from which the elastic composite is derived (e.g., cut from) is driven in an assembly line during manufacturing. The term "cross-machine direction" or "cross-directional," on the other hand, refers to the direction that is transverse to the machine direction. With reference to the elastic composite 210 of FIGS. 2 and 3, the cross machine direction is the direction XX extending laterally relative to the longitudinal line LL. As sometimes described herein, such an elastic composite may be described as a "cross-directional" elastic composite or as exhibiting cross-sectional elastic properties.

The elastic composite band 210 has a central region 214 in which an elastic construction 214 is situated. Extending laterally from this central elastic or elasticized region 214 are regions 216 and 218, which are substantially non-elasticized ("dead zones"). As shown in FIG. 2, the regions 216, 218 occupy the expanse between the central elastic region 214 and the side edges 210a, 210b. Now with reference to FIG. 5, the elastic composite band 210 has a top layer 318 and a bottom or base layer 320. The two layers 318, 320 preferably extend the total width and length of the elastic composite band 210, thereby providing the side edges 210a, 210b, and the end edges 210c, 210d. Both the base layer 320 and the top layer 318 are preferably a non-woven, breathable, disposable material such as propylene, non-woven fabric, breathable polyethylene/polypropylene films, or non-porous films (or combinations of these materials). The base layer 320 and top layer 318 adhere to one another, thereby sandwiching and securing a plurality of elastic strands 322 therebetween.

The elastic strands 322 may be substituted by suitable elastic elements such as elastic strands, threads, ribbons, and elastic glue beads. The elastic elements or strands 322 are distributed along a direction that extends between the side edges 210a, 210b and generally parallel with (or corresponding to) centerline LL. Further, each elastic element 322 is generally aligned or oriented in a direction corresponding with the lateral or cross-machine direction, i.e., in a direction generally perpendicular to the longitudinal center line LL and intersecting the side edges 210a, 210b (i.e., cross-directional). Preferably, the elastic elements 322 are disposed in generally parallel relation and spaced apart generally equally along the longitudinal direction. More preferably, the elastic elements 322 are of generally equal length. Accordingly, when the elastic composite band 210 is worn, the elastic elements 322 impart elasticity to the structure which allows the band 210 to stretch in the lateral or cross-machine direction XX. Because the elastic elements 322 are independent, spaced apart and maintained along the generally lateral direction, the stretch and contraction of the elasticized material are generally cross-directional. This alternative may be functionally and aesthetically advantageous in some garment applications.

Figure 3:
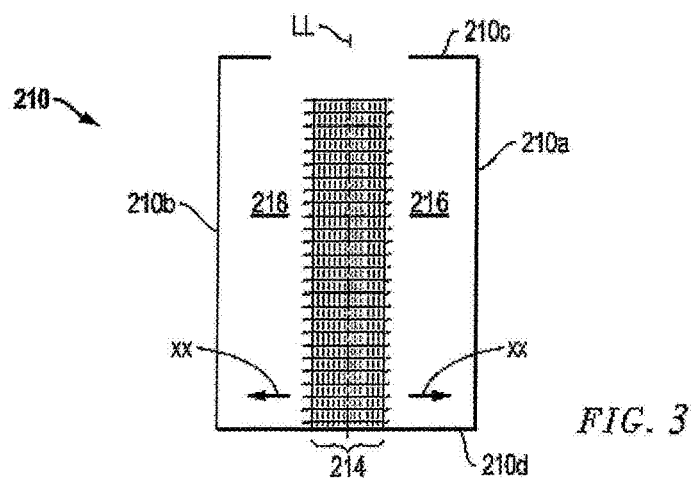
FIG. 3 is a plan view of the elastic composite of FIG. 2 shown in an extended, stretchable condition.

The elastic elements 322 are preferably tensioned during securement between the top and base layers 318, 320. FIG. 3 illustrates the elastic composite band 210 in a laterally stretched condition. In this condition, the central elastic region 214 has a width that is almost equal to the non-elasticized zones 216 and 218. When returned to the non-laterally stretched or relaxed condition, as shown in FIG. 2, the central elastic region 214 contracts and crimps to a substantially reduced width. In this condition or state, the contracted elastic elements 322 shirrs the elastic composite 210 and provide pleats 234 in the contracted elastic region 214.

Returning to FIG. 1, the disposable absorbent garment 110 employs one or more elastic composite bands, as described above. The disposable absorbent garment 110 employs in each of the ear portions 118, a fastening tab 124 having an elastic composite construction. As the fastening tab 124, the elastic composite band is configured such that one non-elasticized region 124a is attached to and overlaps the central body 120 of the garment 110 while a second non-elasticized region 124b is situated outboard of the side margins 144, 146. An elasticized region 124c provides elasticity in the lateral or cross-machine direction (of the elastic composite). In respect to the rest of the garment 110, the elasticity or stretch provided by the central elastic region 124c directed along a direction that is generally perpendicular to the longitudinal center line AA of the garment 110, and corresponds with a direction that wraps about the waistline of the user.

The disposable absorbent garment 110 in FIG. 1 also provides an elastic composite, as the waistband 130. The waistband 130 is situated centrally in the waist region 114. Further, the elastic composite waistband 130 is disposed such that non-elasticized regions 130a, 130b are positioned outwardly of the longitudinal line AA of the garment 110, while an elasticized region 130c is positioned centrally across the longitudinal center line AA. Moreover, the elasticized region 130c is configured such that the elastic strands are aligned or oriented in a direction that is generally perpendicular to the longitudinal centerline AA. In this way, the elastic composite waistband 130 imparts elasticity about the waist region 114 of the garment 110, and in a direction corresponding with the direction of waistline about the user.

FIG. 4 depicts an alternative disposable absorbent garment 410. Specifically, FIG. 4 depicts a disposable absorbent garment 410 employing elastic composites as attachable ear portions or side panels 414. The elastic composite side panels 414 are separate components that are attached to a central body 420 of the garment 410. The elastic composite side panels (or ear portions) 414 are attached near one waist edge 442 of the garment 410 and such that the centerline AA of the side panel 414 is generally parallel with the longitudinal centerline AA of the garment 410. Moreover, each of the elastic composite side panels 414 has a non-elasticized region 414a that is positioned outboard of the side margins 446 of the garment 410 and a second non-elasticized region 414b that is attached inboard of the side margin 446 (or side margin 444).

Figure 6:
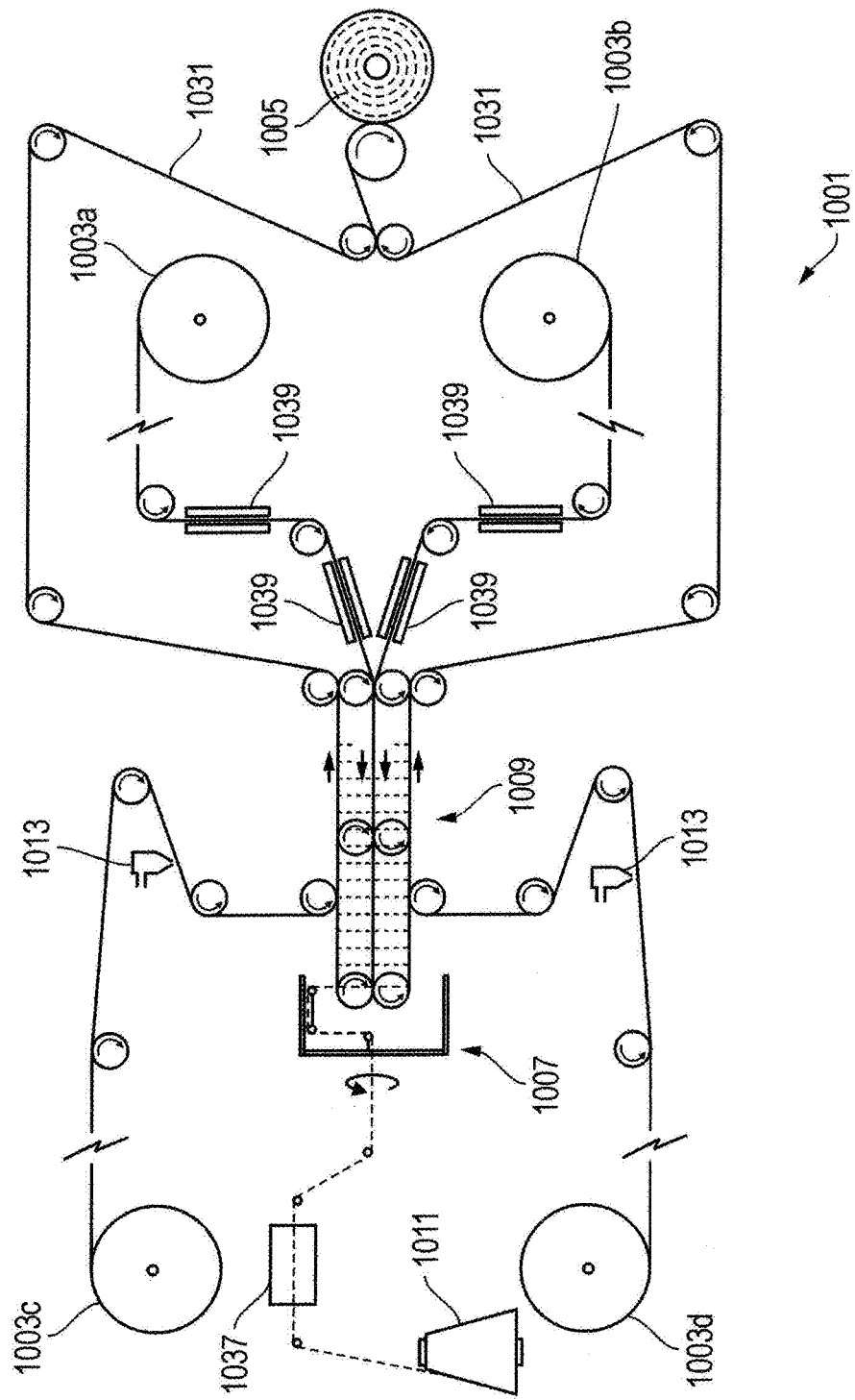
FIG. 6 is a simplified schematic of a system for manufacturing an elastic composite having a dual elasticized region, according to the prior art.

Before describing the elastic composite of the invention, FIGS. 6-10 are provided to illustrate a known system, and system components, and process of making or manufacturing an elastic composite, as previously practiced and described in more detail in U.S. patent application Ser. Nos. 10/733,649 and 11/021,424. In the prior art process illustrated therein, two elastic composite web outputs 1031 are produced from four separate non-woven web inputs 1003a, 1003b, 1003c, and 1003d. Referring first to FIG. 6, a system 1001 includes four separate non-woven web inputs 1003a-1003d, which provide a web or roll of non-woven material for the elastic composite. The system further includes an output assembly or reel 1005 that receives two elastic composite webs 1031 from the rest of the process. These two separate elastic webs may be later fixed together after manufacturing to produce the kind of composite having two elasticized regions.

Central to the system 1001 is a conveyor assembly 1009 for receiving, manipulating, and conveying each of the non-woven web inputs. The conveyor assembly 1009 is positioned and operatively associated with an elastic element applicator such as a spinning head assembly 1007. The assembly 1007 applies elastic fibers or strands upon, onto, and/or integrally with the non-woven web inputs. The spinning head assembly 1007 further includes a spinhead 1017, preferably in the form of a spinning bracket, or cylinder 1017 and the like. The spin cylinder 1017 is configured to hold an "end section" of the continuous strand WW of elastic and move it about a generally vertical plane XX in a reciprocal or repetitive pattern (relative to the conveyor assembly 1009). This plane XX is defined by the area within the spinning perimeter of the cylinder 1017 and which is traced by the outer most bracket or eye 1017b securing the strand of elastic WW to the spin cylinder 1017. The paths of the spinhead 1017 and the section of elastic strand retained thereby are provided on the plane XX.

As shown in the schematic of FIG. 6, non-woven inputs 603a and 603b are fed, utilizing a series of rollers, into the conveyor assembly 1009. Before the two non-woven webs are fed into the conveyor assembly 1009, the webs are directed through the folding guides or plates 1039. The folding guides 1039 serve to effectively reduce the overall width of the non-woven web by folding the lateral or side edges along a pre-determined, longitudinally-extending side fold line YY. The first folding guide 1039*a* initiates the first 90° turn while the second folding guide 1039*b* initiates a second 90° turn. The roller 1039 disposed in between the guide 1039*a*, 1039*b* facilitates the folding process. The two folding guides 1039 and roller 1369 may be referred together as a folding guide assembly.

The conveyor assembly 1009 is set up so as to guide these two non-woven webs 1003*a* and 1003*b* through the center of the assembly 1009 towards and eventually inside the elastic spin cylinder 1007 (into the spinning path). Once inside the spin cylinder 1017 the conveyor assembly 1009 delivers the non-woven webs to each outside, upper and lower faces (outward faces) of the conveyor assembly 1009. At this point, the direction of travel of the non-woven webs is reversed and the webs are directed outward from the spin cylinder 1007. As the non-woven webs exit the spin cylinder 1017, an elastic strand WW is wrapped around the entire conveyor assembly 1009, and as it contacts the upper and lower face of the web platforms it comes into contact with the non-woven web. As shown in several of the Figures, the elastic strand WW is applied crosswise or laterally on the web, and transverse to the direction of the moving web. The friction between the tensioned elastic strand and the non-woven webs on the upper and lower faces of the conveyor assembly draws the "wrapped" elastic strand out of the spin cylinder 1017 and towards contact with two further non-woven webs 1003*c* and 1003*d*.

The non-woven webs 1003*c* and 1003*d* are operatively positioned upstream of an adhesive applicator 1013. Utilizing a system of rollers in conjunction therewith, the non-woven inputs 1003*c*, 1003*d* and adhesive applicators 1013 apply a web of pre-glued non-woven material onto the conveyor assembly 1009 and onto the elastic strand "wrapped" around the non-woven webs 1003*a* and 1003*b*.

Furthermore, the system 1001 employs a standard elastic input source, e.g., a bobbin of elastic yarn, that feeds elastic strands or fibers WW onto a tensioning/speed controlling unit 1037 and then to the spin cylinder or the spinning head 1017, so as to apply the strands WW onto the conveyor assembly 1009 and the non-woven material webs conveyed therethrough. Elastic is taken off the bobbin, box or positive drive system and fed through a tension and speed controlling motor towards the spin cylinder 1017. The elastic WW is delivered through a hollow shaft in the motor controlling the spin cylinder 1017. The elastic WW then passes into the spin cylinder 1017 and is guided by rollers, eyes or any other suitable mechanism around the inside face of the spin cylinder 1017.

Figure 7:
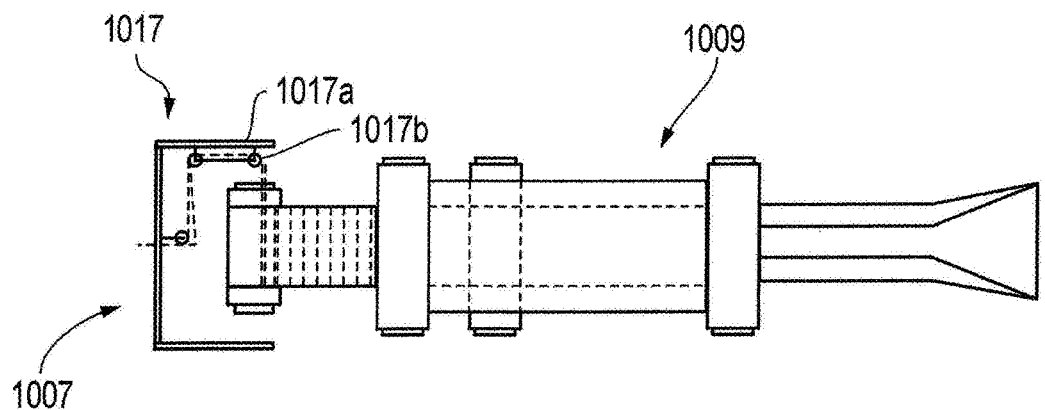
FIG. 7 is a top view of an elastic element applicator assembly for use with the system of FIG. 6.
Figure 9:
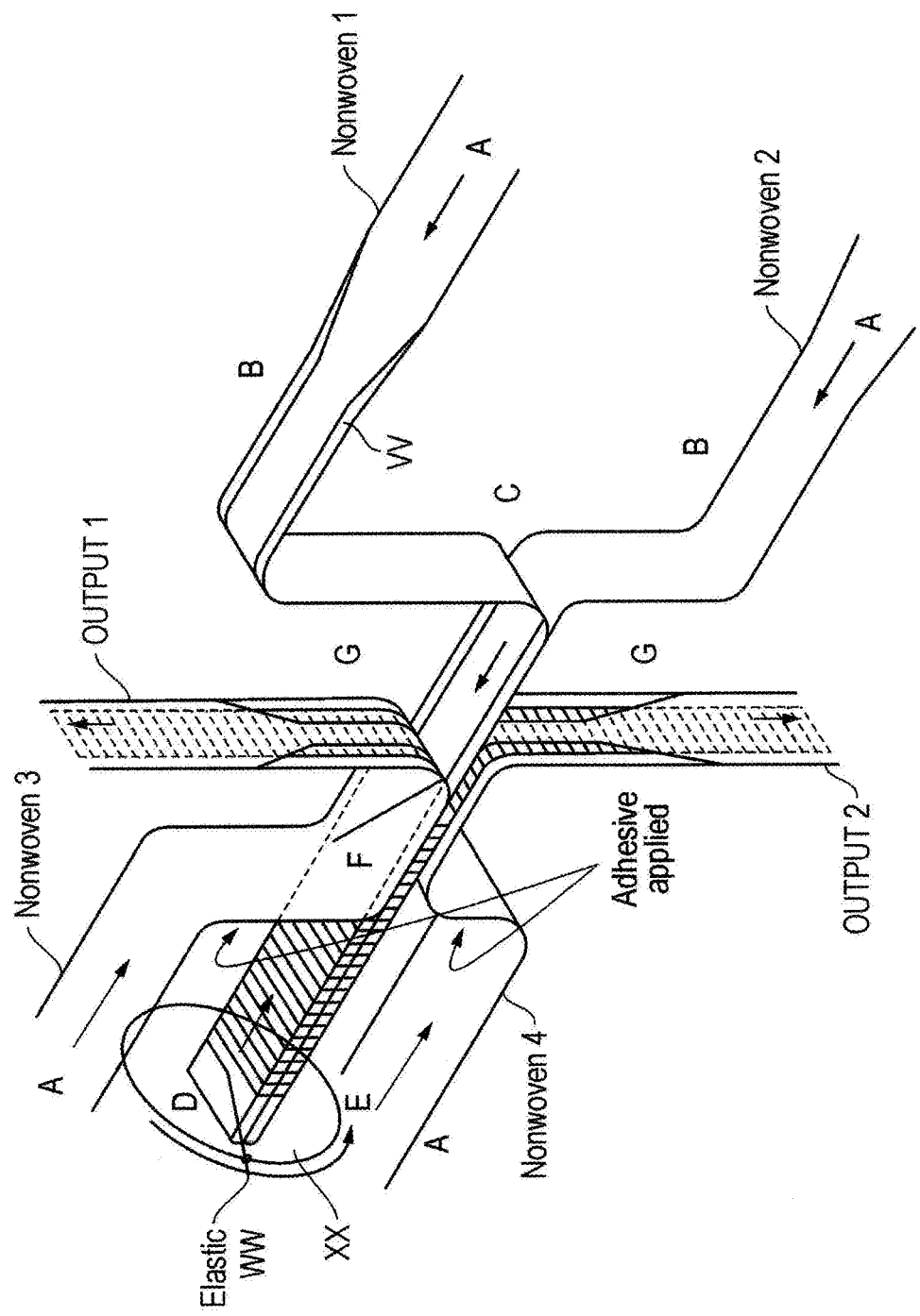
FIG. 9 is a simplified process illustration of making the elastic composite, according to the prior art.
Figure 10:
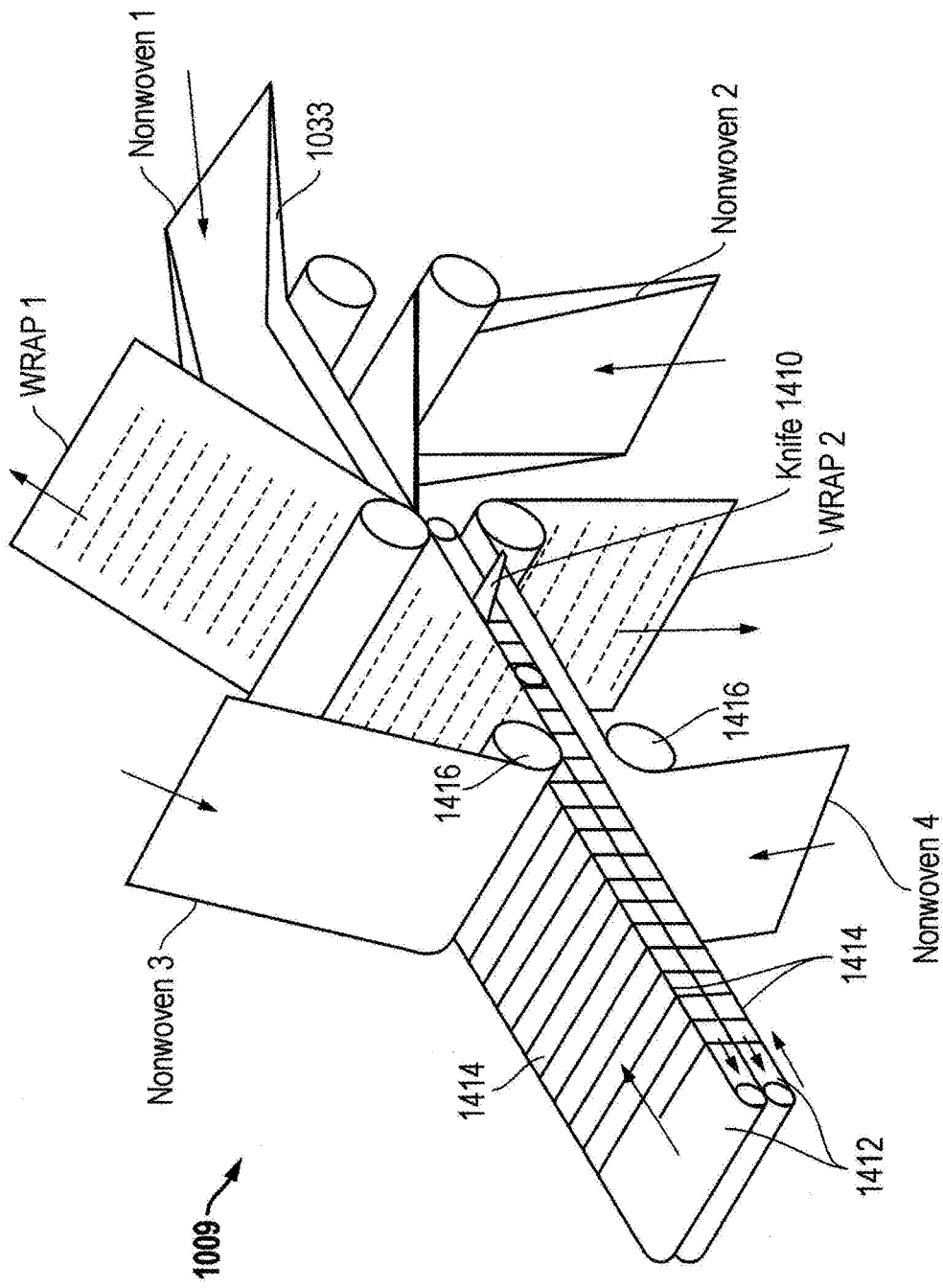
FIG. 10 is a simplified process illustration of making the elastic composite, according to the prior art.

FIG. 7 provides an alternate view of the spinning head assembly 1007 and conveyor assembly 1009. As discussed above, the conveyor assembly 1009 receives four separate webs of non-woven materials and outputs two webs 1031 of elastic composite. FIGS. 9 and 10 are provided to further illustrate the process of making the elastic composite. These figures, more particularly FIG. 9, illustrate the paths taken by the non-woven web materials to and from the conveyor assembly 1009.

Referring to FIG. 9, reference letters A-G are used to refer to stages in the process and in conjunction with the description of the process. As discussed above, non-woven raw material webs are fed into the process at stage A. These webs provide four separate non-woven web inputs into the process. Non-woven webs 1 and 3 are combined to make an elastic composite output 1 (i.e., referred to in the Figures as the WRAP output). Non-wovens 2 and 4, which are both on the downside of the spinning head assembly 1007 and conveyor assembly 1009, combine to make a second elastic composite output 2 (i.e., WRAP 2).

At stage B, non-woven webs 1 and 2 are folded prior to being directed to the conveyor assembly 1009. A predetermined width of non-woven is folded over each side of the web to make two folded flaps VV. The width of the flap VV determines the width of the dead zone or non-elasticized region described previously, while the width of the non-woven, after folding, determines the width of the elasticized region. At stage C, the non-woven webs 1 and 2 are fed into the conveyor assembly 1009, in particular into the middle or inside of the conveyor assembly 1009 with the folded side of each web facing the outside of or away from the conveyor assembly 1009. It should be noted that at this stage C, non-woven webs 1 and 2 are not bonded together. The conveyor 1009 then feeds the non-woven webs 1 and 2 towards the spinning head assembly 1007. At stage D, the non-woven webs 1 and 2 have traveled almost the length of the conveyor assembly 1009 and progresses into the spinning path of spinning head assembly 1007 and intersecting the "spinning" vertical plane XX of the elastic strand WW. Further, at the end of the conveyor assembly 1009, the webs 1 and 2 are directed away from each other and onto the outside of the conveyor 1009 and away from the spinning head 1007. Non-woven web 1 turns up on the upper side of the conveyor assembly 1009, while non-woven web 2 travels along the lower side of the conveyor assembly 1009. At stage E, an elastic strand WW is wound around the folded non-woven webs 1 and 2, as these webs pass through the spinning head and the vertical plane XX. The elastic strand WW is applied to the moving webs 1 and 2 cross-directionally to the direction of the moving web. The movement of the webs 1 and 2 away from within the spin cylinder 1017 draws the "wrapped" elastic strand out of the spin cylinder 1017.

Figure 16:
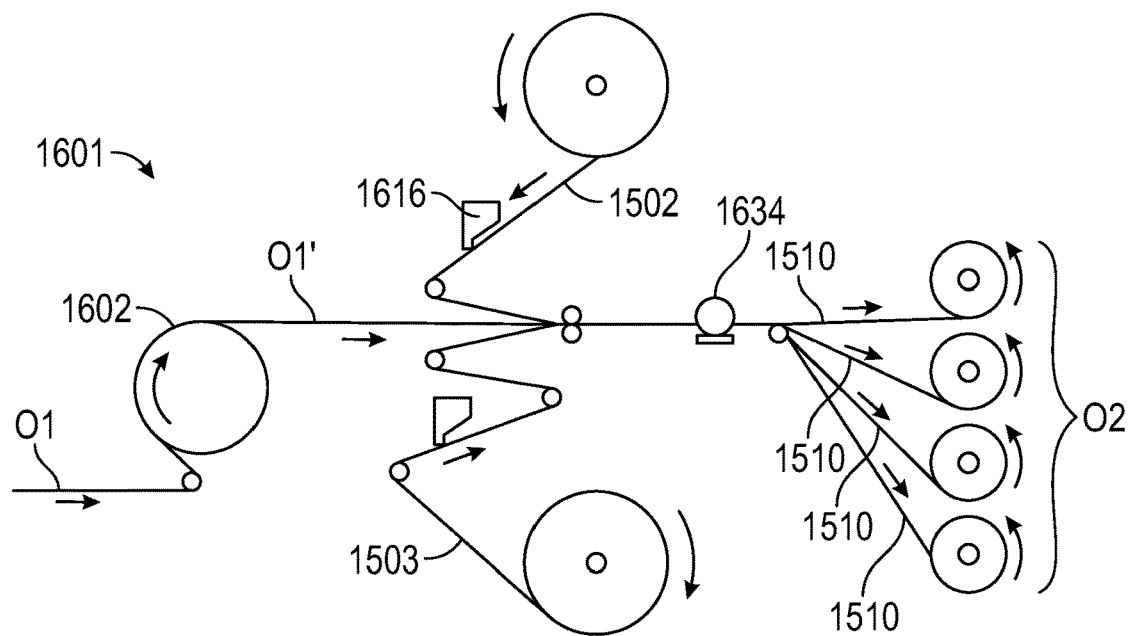
FIG. 16 is a simplified system and process illustration of making the elastic composite in FIG. 15, according to an embodiment of the present invention.

Now turning to non-woven webs 3 and 4, these webs are provided to the conveyor assembly 1009 with adhesive applied on one side (i.e., applied by the adhesive applicator 1013). At stage F, the non-woven webs 3 and 4 are brought into contact with webs 1 and 2, respectively, and the elastic strands WW. As a result, the webs 1 and 3 sandwich elastic strands WW on the upper side of the conveyor assembly 1009, and non-woven webs 2 and 4 sandwich elastic strands WW on the under side of the conveyor assembly 1009. The elastic strands WW run between the two non-woven elastic non-woven composite (cross-direction), but is then cut by a knife (see knife 1410 in FIG. 10, as described below), thereby separating the two wrapped composites. At stage G, the composites 1 and 2 are fed away from the conveyor assembly 1009 and the folded flaps on webs 1 and 2 become unfolded, with guiding, to form a flat non-woven composite. Subsequently, the composites are guided from the spinning head assembly 1007 and conveyor assembly 1009 and into further processes. As shown in FIG. 16, the elastic output webs arrive via a system of rollers onto an elastic composite output reel 1005.

FIG. 10 provides an alternate view of the conveyor assembly 1009. This Figure further illustrates the movement of non-woven webs 1-4 and the application of elastic strands in a generally mutually parallel pattern and generally spaced apart from one another. After cutting of the elastic with the knife 1410, two elastic composites are directed away from the conveyor assembly 1009. It should also be noted that the system advantageously allows for improved control of the stretch of the elastic strands.

Figure 8:
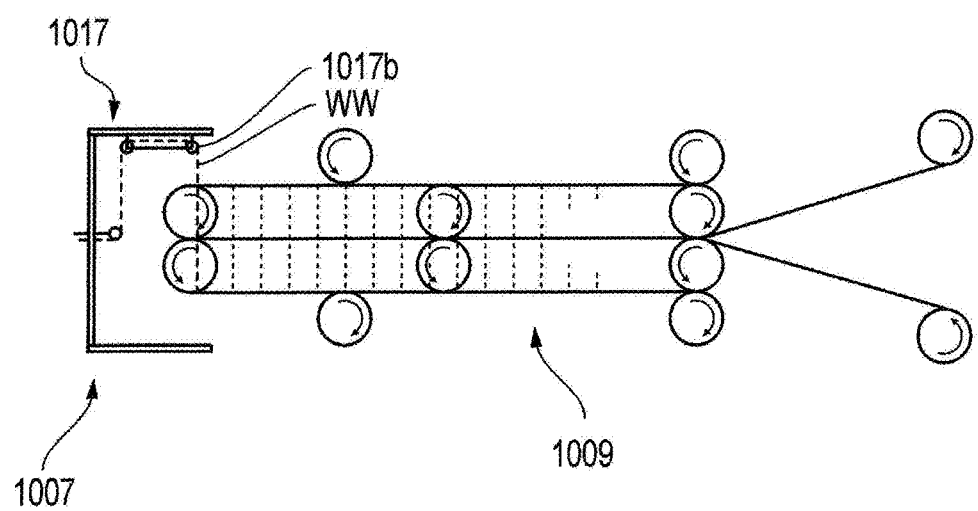
FIG. 8 is a side view of the assembly of FIG. 7.

As shown in FIGS. 8 and 10, the conveyor assembly 1009 includes two web moving platforms 1412 that are juxtapositioned so as to provide an interface therebetween. Each web moving platform 1412 includes a continuous belt 1414 supported about a plurality of rollers 1416 so as to be capable of reciprocal motion. The two web moving platforms 1412 are generally the same length and juxtapositioned so as to accommodate the non-woven webs 1 and 2 therealong from one end to the other end. Preferably, a roller 1416 is situated about midway between the ends of the web moving platform so as to deliver the non-woven webs 3 and 4 respectively to the web moving platform.

As shown in FIG. 6 and also FIG. 10, the spinning head assembly 1007 is positioned about and in the vicinity of one end of the conveyor assembly 1009. In operation, the spinning head 1017 spins about the vertical plane XX which intersects the ends of the web moving platforms 1412 so as to deliver the elastic strands WW around and about both web moving platforms 1412. In operation, the first and second non-woven move along the outside or exposed surfaces or sides of the web moving platforms 1412 and receives the elastic strands WW delivered by the spinning head 1017. By way of its movement away from the spinning head 1017, the moving web draws the continuous elastic strand WW from the spinning head 1017.

By pre-folding the two non-woven webs that are fed to the inside of the conveyor assembly 1009, it is possible to create an elastic composite with cross directional stretch having non-elasticized regions ("dead zones") along each edge. The width of the central elasticized region is fixed to the width of the conveyor platform 1412. The width of the non-elasticized regions or dead zones is determined by the width of the fold VV. The fold VV in the non-woven is preserved by the conveyor assembly 1009 during application of the elastic element and is applied in such a way that the folded edge of the non-woven is not in contact with the elastic element WW. The fold VV is then allowed to open after the composite exits the conveyor assembly 1009 to provide a flat elastic composite with non-elasticized regions. By altering the alignment of the materials as it enters the conveyor assembly 1009 or by changing the widths of the materials used it is possible to create various composite designs.

FIGS. 6-10 and the above accompanying description illustrate a method of making an elastic composite that is different from and precedes the present invention. Most of the steps, sub-processes, components and sub-systems associated with the method may be employed, however, in the systems and methods of the present invention. In fact, applicable detail descriptions of system components and operation may be borrowed from this portion of the specification to illustrate the inventive systems and methods. Differences between the previously disclosed systems and the systems to be described, in respect to the present invention, represent, or arise from, improvements provided by the present invention. Such differences are discussed below in more detail.

The focus of the remaining descriptions shifts now to an alternative and, for some applications, improved system and process for producing an elastic composite having a plurality of mutually spaced-apart elastic elements, and, more preferably, such an elastic composite having cross-directional elasticity. FIGS. 11 through 27 are provided to help illustrate such an elastic composite with cross directional elasticity, and systems and method of making the elastic composite. In further embodiments, the elastic composite has a pair of non-elasticized regions or dead zones and a central elastic region positioned therebetween. Of particular concern is an alternate method of making a continuous web of elastic composite having cross-directional elastic properties, with marked improvements in efficiency, productivity, flexibility, and/or economy. As discussed herein, such an elastic composite according to the preferred embodiment may lend itself to post-processing and integration of the elastic composite into various components of a disposable absorbent article.

As discussed previously, the term "elastic composite" is used to refer to a multi-component material construction that includes elastic elements. In some embodiments, the elastic components include one or more nonwoven layers and elastic elements that impart elasticity on the nonwoven layer(s). In further embodiments, such an elastic composite is in a form suitable for direct integration as a component in a disposable absorbent article. Such an elastic composite may be fed directly into a system and main process for making a disposable absorbent article. In other embodiments, the elastic composite is in a form that is well suited for further processing before integration as a component in a disposable absorbent article. For example, the elastic composite provided herein may be a novel construction that captures the target cross-directional elastic properties of a plurality of elastic elements and provided in a form that facilitates further processing. In one further example, the elastic composite is a novel laminate construction that captures a desired multi-layered elastic construction and in a form that can yield a plurality of individual cross-directional elastic composites in ready form. In other examples, the novel laminate construction is further processed to yield individual cross directional elastic composites having a multilayered central elastic region and, in a further embodiment, a pair of non-elastic regions or dead zones.

With the methods of manufacturing discussed earlier, particularly in respect to FIGS. 6-10, elastic composites preceding the present invention featured a central elastic region having a width that is depended on, and thereby, limited by, certain manufacturing parameters. Specifically, the lateral or cross-directional width of the elastic region in the stretched state is fixed by the dimensions of certain manufacturing components. For example, the diameter of the spin head (and also of the vertical plane XX; see FIG. 9 and accompanying description) imposes a length limitation on the elastic elements in the central elastic region. The spin head encircles the conveyor assembly and thus, the width of the nonwoven web that is supported on the conveyor assembly must be less than the diameter of the spin head. Such a limitation on the length of the elastic element also dictates the minimum width of the nonwoven sheet onto which the elastic element is applied. Similarly, the width of the conveyor that conveys the nonwoven to the spin head, and about which the elastic is wrapped, dictates the practical width of the nonwoven sheet and thus, the length of the elastic elements. Furthermore, the diameter of the spin head is limited by the practical speed of the manufacturing process. In one aspect of the present invention, systems and methods are provided that readily allow for a cross directional elastic composite having a relatively wider elastic region. In yet another aspect, a system and method are provided for varying the width of the elastic region.

Figure 11:
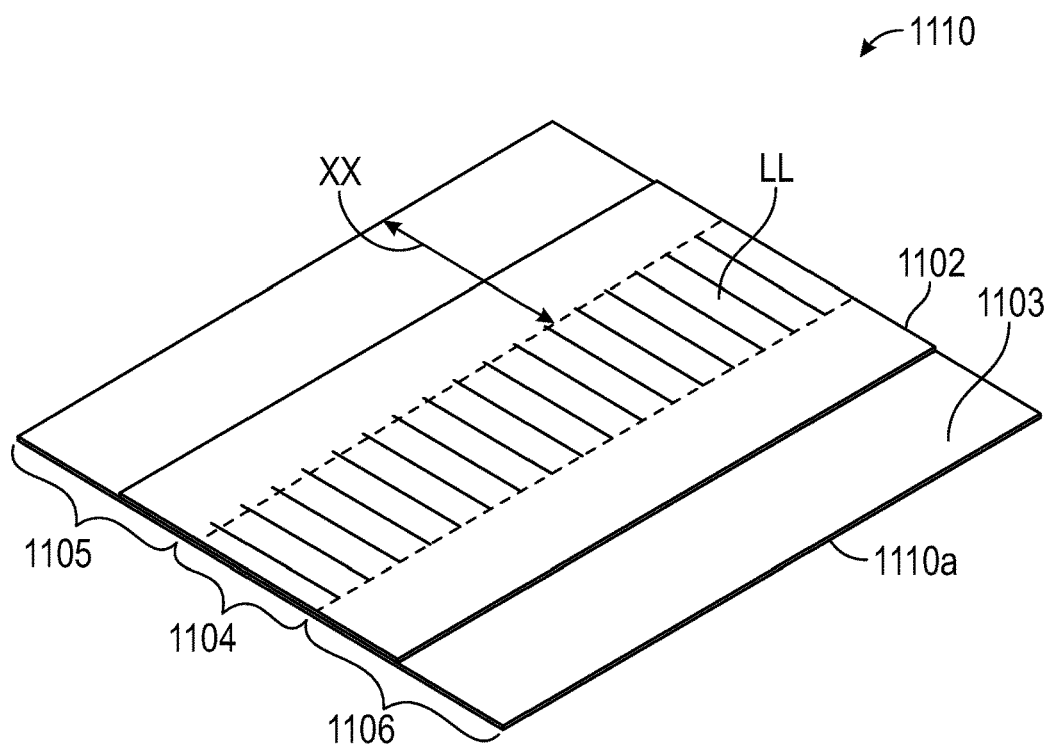
FIG. 11 is a simplified illustration of a prior art cross-directional elastic composite.

To facilitate description of an elastic composite according to the present invention, FIG. 11 is provided to illustrate a type of elastic composite 1110 of which the present invention is directed (see also FIGS. 2A, 2B, and 3). The conventional elastic composite 1110 has a central elastic region 1114 in which an elastic construction 1114 is situated and non-elastic regions (dead zones) 1105, 1106, each aside the central elastic region 1114. The elastic composite 1110 is composed of an upper nonwoven layer 1102, a lower nonwoven layer 1103, and a plurality of mutually spaced apart elastic elements 1101 sandwiched therebetween. The plurality of elastic elements 1101 are positioned centrally and are aligned generally laterally, preferably generally perpendicular to a longitudinal centerline LL of the elastic composite 1110. Preferably, the elastic elements 1101 are strands that are tensioned when applied to the nonwoven layers 1102, 1103 so that the nonwoven layers are later gathered by the elastic elements 1101 as the elastics relax.

Figure 12:
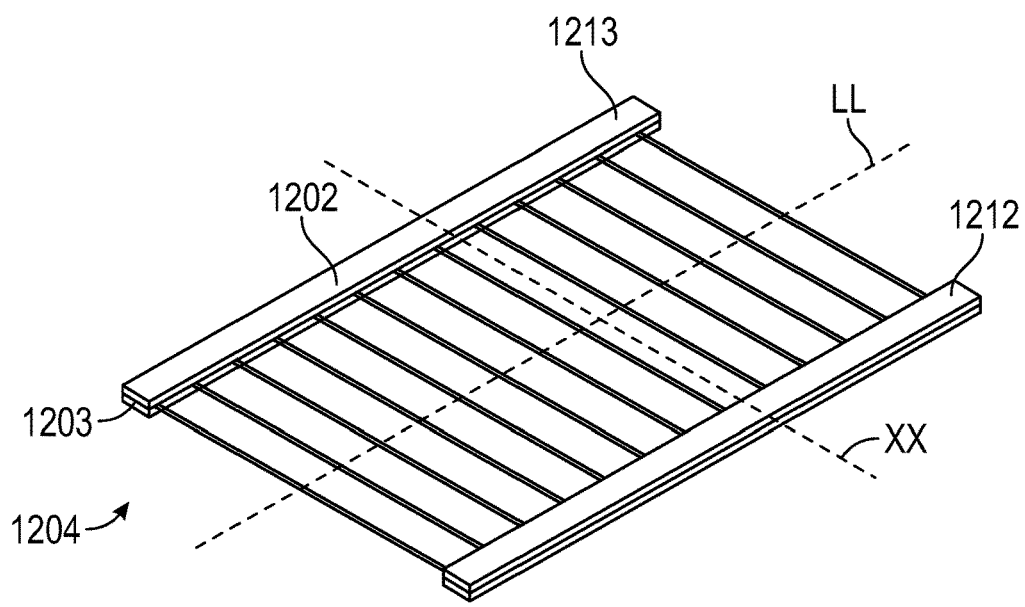
FIG. 12 is a simplified illustration of a cross-directional elastic composite according to a preferred embodiment of the present invention.

FIG. 12 depicts an elastic composite 1210 in accordance with a preferred embodiment of the present invention. In one respect, the elastic composite 1210 features the same basic construction as the previous elastic composite 1110: a multi-layered, cross-directional elastic composite 1210 with a central elastic region 1204 and a plurality of mutually spaced apart elastic elements 1201 in the central elastic region 1204. The plurality of elastic elements 1201 provides, at least in this embodiment, a central elastic region 1204 that is clear of nonwoven layers. The elastic elements 1201 are, therefore, exposed and define an open elastic area or region 1204. Furthermore, the elastic region 1204 is situated in between a first nonwoven composite carrier 1212, and a second nonwoven composite carrier 1213 (hereinafter "carriers"). Each of carriers 1212, 1213 is preferably composed of a first or upper nonwoven layer 1202, a second or lower nonwoven layer 1203, and the ends of cross directional elastic elements 1201 sandwiched therebetween. In further embodiments, the upper and/or lower layers may employ a sheet material other than woven (e.g., a film). The carriers 1212, 1213 are spaced in the lateral or cross machine direction XX from a longitudinal centerline or machine direction LL of the elastic composite 1210. In this preferred embodiment, the carriers 1212, 1213 are placed generally in parallel relation with the centerline LL and provide the side border of the elastic composite 1210. More preferably, the open elastic region 1204 is generally centered about the composite centerline LL, and the elastic elements 1201 are equally spaced and centered about the longitudinal centerline LL in generally perpendicular relation.

A comparison of the elastic composite 1210 with the earlier elastic composite 1110, as depicted in FIG. 11, reveals at least a few important physical distinctions. A primary feature of the elastic composite 1210 is that the elastic elements 1201 are substantially uncovered or revealed between the carriers 1212, 1213. Moreover, the three-layered composite, which is now referred to as carriers 1212, 1213, has a substantially reduced width as compared to the width of the elastic region 1204. As will be further described, the nonwoven carriers 1202, 1203 serve primarily to hold elastic elements 1201 in place (even if only temporarily) and facilitate further processing of the elastic composite.

Figure 13A:
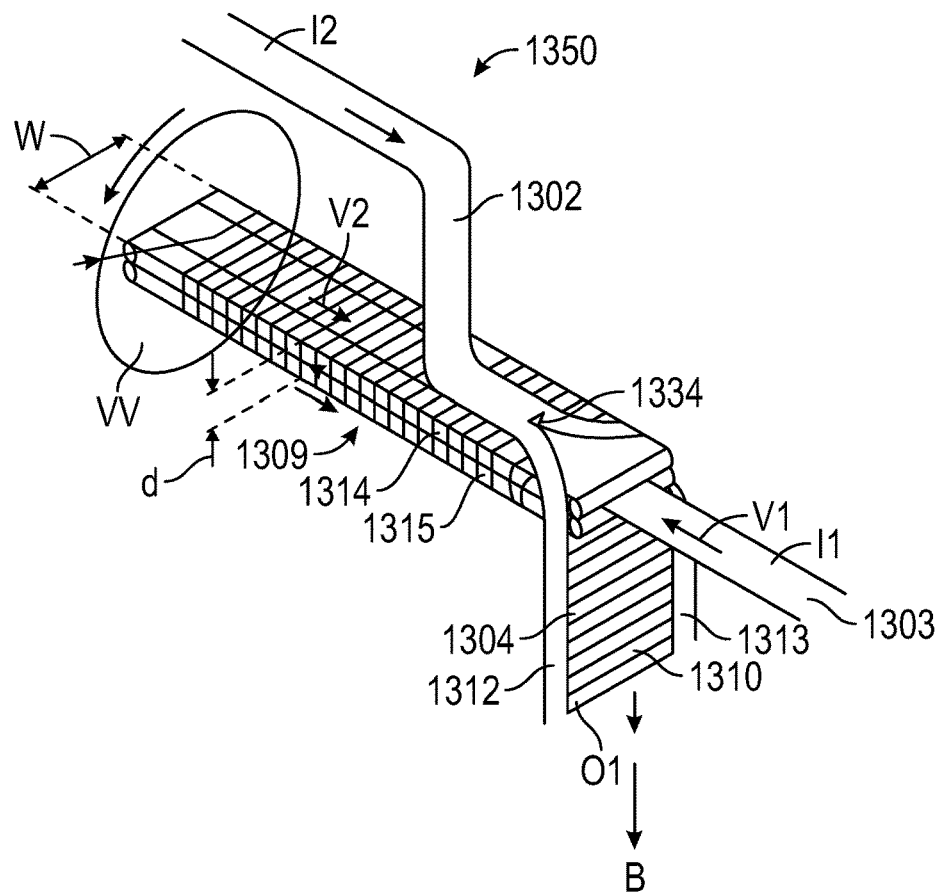
FIG. 13A is a simplified process illustration of a system and method of making the elastic composite in FIG. 12, according to a preferred embodiment of the present invention.
Figure 13B:
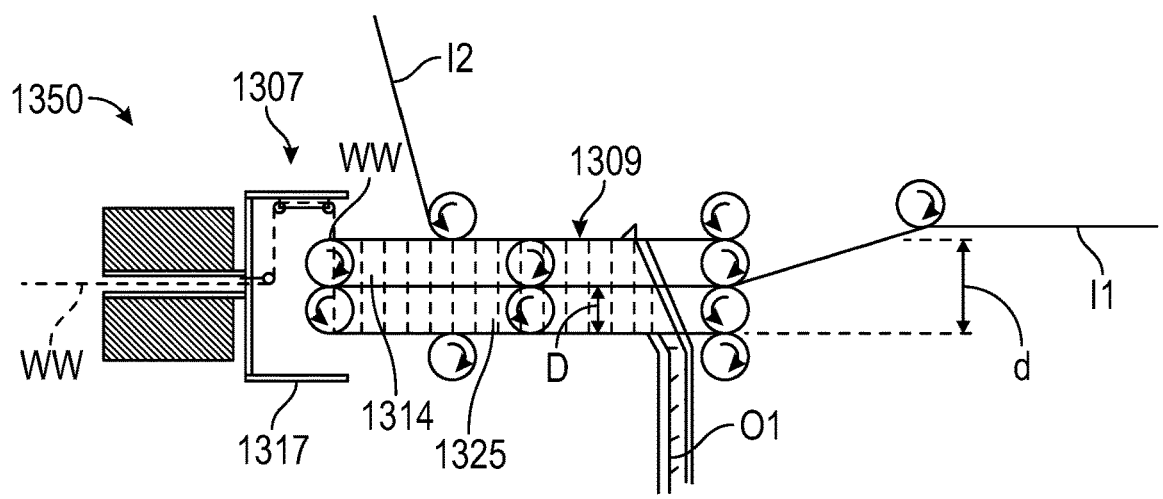
FIGS. 13B-C are simplified illustrations of a system of making the elastic composite in FIG. 12, according to a preferred embodiment of the present invention.
Figure 13C:
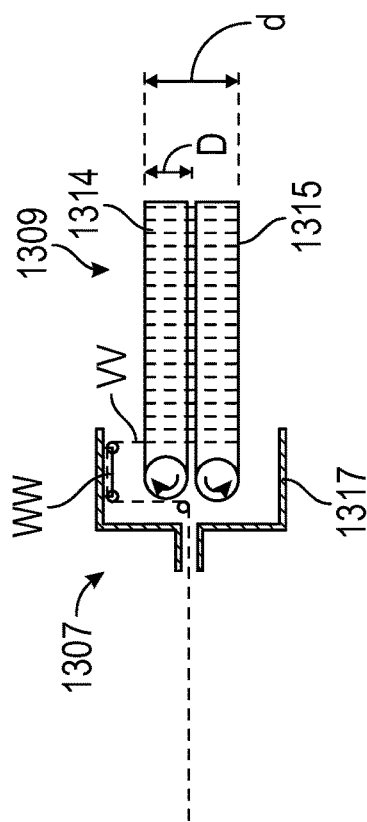

FIGS. 13A-13C are simplified illustrations used herein to describe an exemplary system and process for making the elastic composite 1210, according to a preferred embodiment of the invention. Suitable components for the system and apparatus shown in FIGS. 13A, 13B, are substantially the same as or equivalent to those previously described herein (FIGS. 6-10). Moreover, the function and operation of the components have also been described previously or are generally known in the art. Accordingly, details as to the configuration and operation of these components are not provided herein, but will be apparent to those skilled in the art.

A system 1350 suitable for the preferred embodiment includes a first nonwoven input I1 (or other suitable material), a second nonwoven input I2 (or other suitable material), and a web output O1 of a continuous elastic composite 1310 according to the preferred embodiment. The first nonwoven input I1 provides or feeds a web or roll (not shown) of a first nonwoven layer 1303 (or other sheet of material), while the second nonwoven input I2 provides or feeds a web or roll (not shown) of a second nonwoven layer 1303. The nonwoven layers 1302, 1303 ultimately provide upper and lower composite layers for each of the two carriers 1212, 1213 of the elastic composite 1310. The system 1350 further includes an output assembly or reel (not shown) to receive the continuous web of elastic composite 1310 or output O1 and, in some applications, direct the output O1 into a main manufacturing process.

Central to the system 1350 is a conveyor assembly 1309 for receiving, manipulating, and conveying the nonwoven web inputs I1, I2 as well as the elastic composite output O1. As described previously, the conveyor assembly 1309 preferably includes an upper conveyor and platform (hereinafter upper conveyor 1314) and a lower conveyor and platform (hereinafter lower conveyor 1315). Referring to FIG. 13C, the two conveyors 1314, 1315 are placed substantially adjacent each other but still sufficiently spaced apart to allow independent movement. Preferably, the two conveyors 1314, 1315 have substantially the same dimensions of length, L, width, W, and depth, D, and are positioned in parallel relation such that one substantially mirrors the other. The vertical distance from the top or outside of the upper conveyor to the bottom or outside of the lower conveyor is the dimension "d". In most prior applications, this dimension, d, is equal to (twice the width, W) plus the gap or distance between the conveyors.

The conveyor assembly 1309 is operatively associated with a suitable elastic element applicator such as a spinning head assembly 1307 and spin head 1317 ("elastic spinners"), as described previously. The spin head 1317 extends slightly over and about the ends of the two conveyors 1314, 1315, and is configured to hold an "end section" of a continuous elastic strand WW of elastic. Revolution of the spin head 1317 moves the end section about a generally vertical plane VV and about the conveyor assembly 1309. The vertical plane VV preferably has a diameter that is just slightly less than the inside diameter of the spin head 1317. The vertical plane intersects the conveyors 1314, 1315 and further, webs moving on the conveyors 1314, 1315. As generally known, the two conveyors 1314, 1315 reciprocate such that the inside platform surface moves linearly toward and past the vertical plane VV in a first web moving direction V1, before turning as the outside platform surface. The outside platform surface moves linearly past the vertical plane VV in a second web moving direction V2 that is the reverse of the first web moving direction V1. The path of the outside platform surface is spaced outwardly of the path of the inside platform surface and in generally parallel relation therewith.

In accordance with a preferred embodiment, a first nonwoven carrier web 1303 is directed to the conveyor assembly 1309. The conveyed web 1303 is then conveyed by the upper conveyor 1314 along the first web moving direction V1 and through the vertical plane VV. After arriving at the end of the conveyors 1314, 1315, the nonwoven carrier web 1303 is passed onto the top conveyor 1314 as shown in FIG. 13A, (or, onto the bottom conveyor 1315 in alternate embodiments). As the nonwoven carrier web 1303 is conveyed through the vertical plane VV, a section of the elastic strand WW is applied across the nonwoven carrier web 1303. Actually, the spin head 1317 revolves about the conveyors 1314, 1315 and wraps a section of elastic strand WW about the two conveyors 1314, 1315.

Noting that the section of elastic WW is applied across the outside surface of the lower conveyor 1315 as well, the moving conveyors 1314, 1315 draw continuous strand WW away from the spin head 1317. The new substrate now consisting of the nonwoven web 1303 and the elastics applied thereon is subsequently met by a second nonwoven web 1304. The second nonwoven web 1302 is directed onto and in union with the upper conveyor 1315a and atop the substrate of the first nonwoven web 1303 and elastics applied thereon. As generally known, the second nonwoven carrier web 1304 is preferably applied with a process adhesive upstream of the upper conveyor 1315a. The adhesive is sufficiently applied to provide a secure bond between the two nonwoven carrier webs 1302, 1303 and the elastics therebetween. In alternate embodiments, another suitable process or means of bonding the layers and elastics may be employed (e.g., thermal bonding, ultrasonic bonding, embossing, etc.)

Thus, a new composite or subcomposite is provided as a result of the union of several components. This union includes: a first nonwoven web 1303 supported on the outside surface of the upper conveyor 1314; a section of elastic strand WW applied across the first nonwoven web 1303 multiple times; and a second nonwoven web 1302 applied atop the first nonwoven web 1303 and the elastics applied thereon. As shown in FIG. 13A, the section of elastic strand WW extends outward from one side of the first non woven web-second non woven web sandwich (on the upper conveyor 1314) (the "union"), wraps around the lower conveyor 1314, and encircles by returning into the sandwich or union through an opposite side. Prior to cutting, the section of elastic strand WW actually encircles or enwraps both conveyors 1314, 1315 and the first nonwoven web 1303 multiple times. Although the lower conveyor 1315 does not convey a sheet of material in the traditional way, it does support and convey (in the web moving direction V2) a series of elastic segments (of the elastic strand WW).

Referring specifically to FIG. 13A, this new composite is moved further in the second web moving direction V2 by both the upper conveyor 1314 and the lower conveyor 1315. The composite is specifically directed to a cutting or slitting mechanism ("slitter" 1334) positioned generally centrally and jutting into the path of the upper conveyor 1314. The moving composite intersects the slitter 1334 and is slit preferably longitudinally across the center of the nonwoven-elastic-nonwoven sandwich ("elastic sandwich"). The elastic sandwich is divided to create the two carriers 1312, 1313 and an open or exposed elastic region 1304 therebetween. The section of continuous elastic strand WW, which had encircled or enwrapped the conveyors 1314, 1315, is also severed to create separate elastic segments 1301. The resulting composite 1310 moves forward, which causes the two carriers 1312, 1313 to slide downward off the conveyors 1314, 1315, as shown in FIG. 13A. Preferably, the carriers fall and unwrap below the conveyor assembly 1309. By slitting the previously enwrapped elastic composite, the resulting composite output O1 may be readily removed from the conveyor assembly 1309 and further received for storage or post-processing.

In one aspect of the preferred embodiment, an elastic composite 1210 is provided having an exposed elastic construction or open elastic region 1204 formed by the plurality of mutually spaced apart elastic elements 1201, as shown in FIG. 12. In this composite 1210, the elastics 1210 of the exposed or open elastic region 1204 are independent or clear of any nonwoven layers. The elastic elements 1201 extend generally laterally from one carrier 1212 to the second carrier 1213, and across the longitudinal centerline LL. The elastic elements 1201 are therefore generally oriented along the cross-machine direction, and may be referred to as cross-directional elastics. Interestingly, the width of the open elastic region 1204 (i.e., the lateral spacing between the two carriers 1212, 1213) is primarily dependent on two processing parameters. Firstly, the width of the open elastic region 1204 is dependent on the total circumference of the conveyor assembly 1309, i.e., the circumference about the upper conveyor 1314 and the lower conveyor 1315. This circumference is also substantially equal to the travel length of the section of elastic strand WW about the conveyor assembly 1309 upon one revolution of the spin head 1317. This length is the sum of the width W of the upper conveyor 1314, the width W of the lower conveyor 1315, and twice the distance, d, between the upper surface of the upper conveyor 1314 and the lower surface of the lower conveyor 1315. Secondly, the width of the open elastic region 1204 is dependent on the tension applied to the elastic strand WW when the strand is applied about the nonwoven web 1303. If a relatively higher tension is applied, the width of the open elastic region 1204 in the relaxed state will be decreased.

Figure 14:
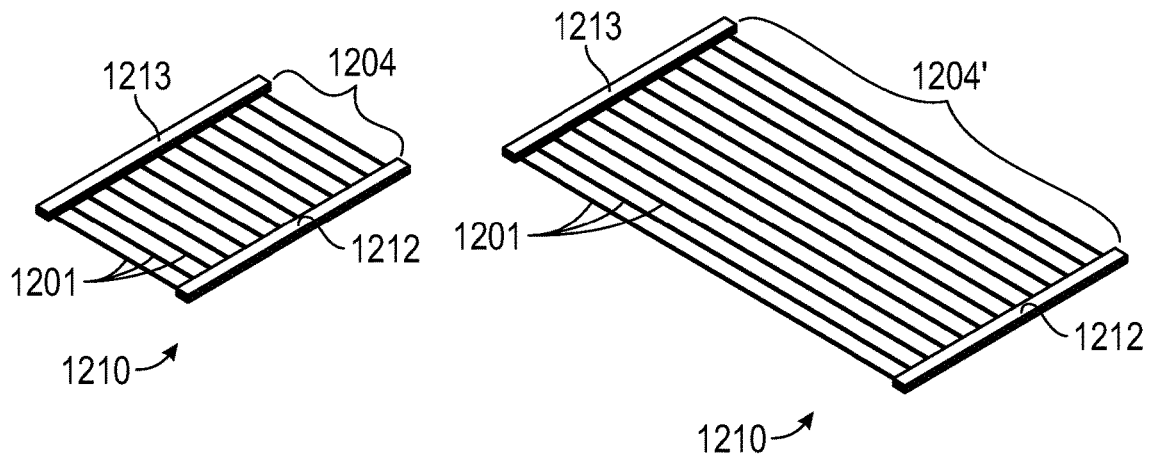
FIG. 14 are comparative illustrations of the elastic composite in FIG. 12 in a relaxed state and in an extended state.

The width of the open elastic region 1204 is also dependent on and provided by the extension state of the elastic elements when the measurement is taken. Generally, the important reference measurements are those made when the elastic elements are fully relaxed (extension factor equals 1×), and measurements taken when the elastic elements are fully extended (typical extension factor equals 4× to 6×, depending on the type of elastic used). FIG. 14 illustrates an elastic composite 1210 in a relaxed state, i.e., no tension is applied to the elastic. To the right of the relaxed elastic composite 1210 is a depiction of the elastic composite 1210' under tension, i.e., the extended state.

EXAMPLE 1

In one embodiment of the invention, the width of open elastic region may be approximated as follows:

Given, conveyor width, W=100 mm;
distance, d, from upper surface of upper conveyor to lower surface of lower conveyor=40 mm;
extension applied to continuous elastic strand=4×;
full extension of elastics=5×.

Width of open elastic region (fully extended) =

$$5 \times ((100 \text{ mm} + 100 \text{ mm} + (40 \text{ mm} \times 2))/4) = 350 \text{ mm}$$

Width of open elastic region (relaxed) =

$$(100 \text{ mm} + 100 \text{ mm} + (40 \text{ mm} \times 2))/4 = 70 \text{ mm}$$

EXAMPLE 2

In a more preferred embodiment, the width of the open elastic region is increased by reducing the extension applied to the elastic strand as it is applied to the nonwoven carrier web. The circumference of the conveyor assembly is also increased by increasing the separation of the upper and lower conveyors. In some suitable systems, one of the conveyor platforms is simply moved further from the other platform. It should also be noted that one of the conveyors is not required to move a sheet of material, but only the elastic wrapped about it. This allows for use of conveyors different from the generally flat platforms or belts commonly used to support a sheet of nonwoven.

Given, conveyor width, W=100 mm,
distance, d, from upper surface of upper conveyor to lower surface of lower conveyor=100 mm,
extension applied to elastics=1.5×,
full extension of elastics=5×.

Open elastic region (fully extended) =
$$5 \times ((100 \text{ mm} + 100 \text{ mm} + (100 \text{ mm} \times 2))/1.5) = 1333 \text{ mm}$$

Open elastic region (relaxed) =
$$(100 \text{ mm} + 100 \text{ mm} + (100 \text{ mm} \times 2))/4 = 267 \text{ mm}$$

Examples 1 and 2 above illustrate that the width of the open elastic area may be adjusted by making small changes to the applied extension of the elastics and to the dimensions of the conveyor assembly. In certain embodiments, the tension is determined by the feed rate of the elastic strands into the spin head and the frictional characteristics of the feeding and spinning process. The circumference can be varied mechanically by changing the distance between the upper and lower conveyors.

Notably, the elastic composite 1210 is characterized by mutually spaced apart, cross-directional elastic elements 1201 that extend laterally between the first and second carriers 121, 1213 and in transverse relation with the machine direction of the elastic composite (LL). Each of the layers 1202, 1203 of the carriers 1212, 1213 preferably extends generally longitudinally in generally parallel relation with the machine direction LL and has a lateral width that is substantially less than a lateral width between the first and second carriers 121, 1213 (across the open elastic region 1204). In a further aspect, the elastic elements 1201 of the open central elastic region 12104 are "discrete disconnected segments of one elastic strand". This means that the elastic elements 1201 originate from the same elastic strand and are, in fact, severed sequentially from the same elastic strand while that strand is in a generally uniform state of tension or application (e.g., secured in tension between adhered nonwoven layers). Being discrete disconnected segments of one elastic strand further means that the elastic elements have substantially identical material and mechanical properties (particularly, dimensions, strength, and elastic properties). The inclusion of such elastic elements can offer benefits in the ultimate elastic composite as well as the processes in the making of the elastic composite. For example, having uniformity and consistency in the plurality of elastic elements facilitates handling of the elastic composite, provides a cleaner and more aesthetically pleasing gathering in the ultimate disposable absorbent article, and may also produce a better quality product with less flaws.

Exemplary Applications—Post Processing

A variety of applications for the cross directional elastic composite 1210 and output composite 1303, O1 described above are contemplated. These applications include direct incorporation of the elastic composite 1210 (having the open elastic region) as a component in a disposable absorbent article and particularly, into a process of making the article. For example, the elastic composite 1210 may be integrated as a wide elastic waistband of a diaper type product. The elastic composite 1210 may also be applied as a body encircling elastic component for training pants.

Figure 15:
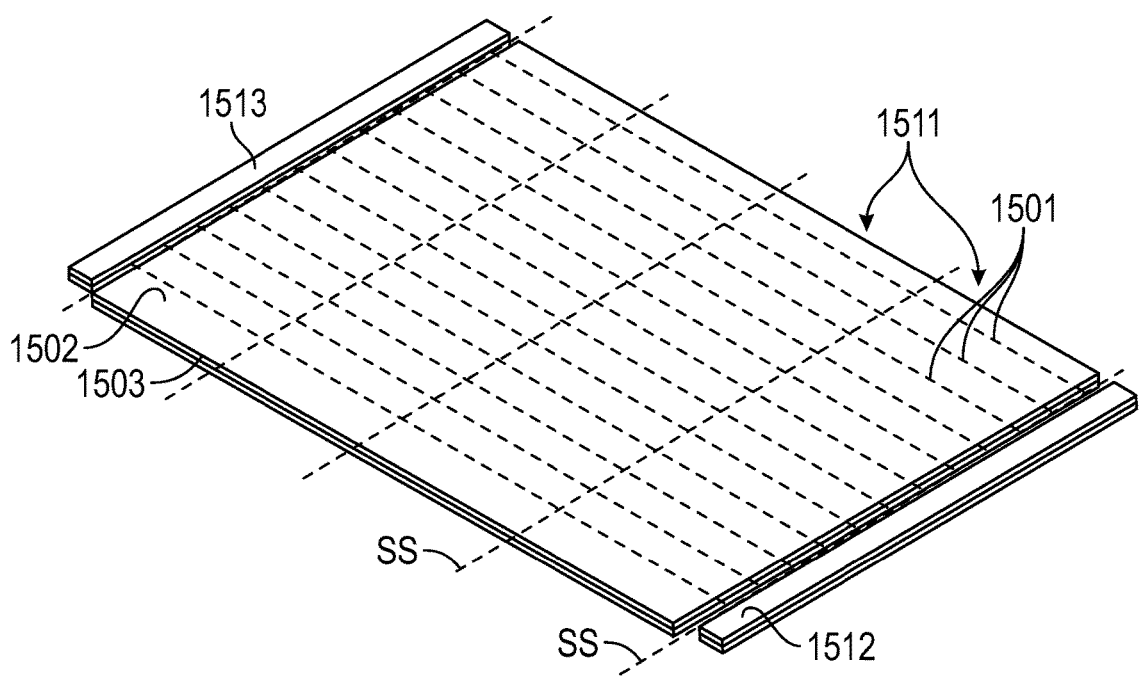
FIG. 15 is a simplified illustration of yet another elastic composite according to an embodiment of the present invention, in the form of an elastic laminate.

A cross directional elastic composite with open elastic region is also well suited for further processing prior to integration into a disposable absorbent article. FIGS. 15 and 15A depict an exemplary product of further processing of elastic composite 1310. FIG. 15A depicts an elastic composite in the form of an elastic laminate 1511 derived from a method according to an embodiment of the invention. The laminate 1511 includes an upper nonwoven layer 1502, a lower nonwoven layer 1503, and a plurality of tensioned elastic elements 1501 sandwiched therebetween. The laminate 1511 further includes first and second carriers 1512, 1513 serving as the side borders of the laminate 1511. The elastic laminate 1511 may yield, in turn, several multi-layered, cross directional elastic composites 1510. These elastic composites 1510 are also in a form that is particularly suited for further processing and ultimately, for fastening tape and elastic side panel applications. FIG. 16 illustrates an exemplary system 1601 and process that receives the elastic composite web output O1 and further processes the web O1 to produce the elastic laminate 1511 and the multilayered elastic composites 1510. In particular, the exemplary system 1601 and process illustrates the flexibility of various embodiments of the invention to create cross-directional elastic sheet materials of varying width.

Figure 17:
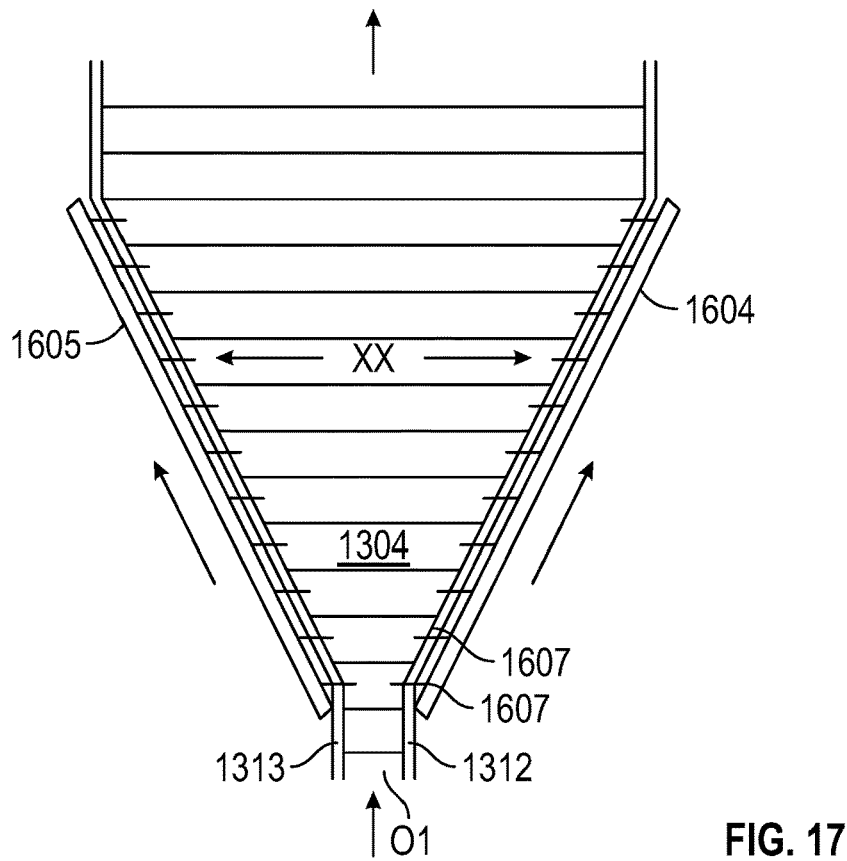
FIG. 17 is a simplified illustration of an extender subsystem suitable for use with the system and process illustrated in FIG. 16.

In accordance with a preferred method, the output O1 (continuous web of elastic composite 1310) of system 1350, as described in respect to FIG. 13, is received by the present system 1601 and more particularly, by a conveying device, referred to hereafter as extender 1602. The extender 1602, shown in further detail in FIG. 17, secures the continuous web O1 along each carrier 1312, 1313 and stretches the open elastic region 1304 to a desired width, while moving the web O1 forwardly in the system 1601. The extender 1602 includes a pair of identical reciprocating components 1604, 1605. The reciprocating components 1604, 1605 may employ a wheel, belt or chain based system to reciprocate. As shown in FIG. 17, the two reciprocating components 1604 are situated upright and spaced apart from another at an angle such that a lateral space XX between the two expands along the web moving direction. The reciprocating components 1604, 1605 are adapted with engagement means 1607 for securing the web O1 preferably at the carriers 1312, 1313. The engagement means can be found in the form of pins, mechanical grips, or the like. The web O1 is stretched as the web O1 is moved forwardly between the two components 1604, 1605 and as the lateral space XX expands. In this way, the extender 1602 extends the width of the open elastic region 1304 to a target width, and carries the elastic web O1 from its original relaxed state to a desired extended or tensioned state (O1').

The tensioned elastic composite O1' is then fed to a laminating stage, wherein a lower nonwoven web 1503 is continuously directed to the web O1' from below and an upper nonwoven web 1502 is continuously directed to the web O1' from above. Prior to reaching the web O1', hot melt adhesive is applied to each of the nonwoven webs 1502, 1503 using suitable adhesive application equipment 1616. Thereafter, the lower nonwoven web 1503 is applied to the "underside" of open elastic region 1504' of the web O1' and the upper nonwoven web 1502 is applied to the "topside" of the open elastic region 1504'. The applied adhesive ensures proper bonding between the nonwoven layers and the tensioned elastic elements. The resulting laminate 1511 includes, therefore, an upper nonwoven layer 1502, a matching lower nonwoven layer 1502, 1503, a pair of carriers 1512, 1513 providing the side borders of the laminate 1511, and a plurality of mutually spaced apart elastic elements 1501 extending between the carriers 1512, 1513 and sandwiched between the nonwoven layers 1502, 1503. As compared to the output web O1, the elastic elements 1501 are now in an extended state, but remain laterally oriented, thereby imparting cross-directional elasticity to the laminate 1511.

Notably, the two carriers 1512, 1513 serve a handling function during the process. The carriers 1512, 1513 ensure that the configuration of elastic elements is maintained as the webs O1, O1' are processed. The carriers 1512, 1513 also provide a solid base for the components of the system 1601 to secure and handle (e.g., convey and stretch) webs O1, O1'.

As shown in the exemplary diagram of FIG. 16, the resulting laminate 1611 is directed forward to a slitting mechanism 1634. In this embodiment, the slitting mechanism(s) includes five slitters that sever the carriers 1512, 1513 from the laminate 1511 and slits the laminate 1511 into four separate webs of yet another cross-directional elastic material or multilayer elastic composite 1510 according to an embodiment of the inventions. The slitters 1634 are positioned in alignment with slitting lines SS along the web O1'. In this embodiment, the set of five slitting lines SS is equally spaced apart and include slitting lines SS adjacent the carriers 1512, 1513. As a result, the slitters 1634 divide the laminate 1511 into four separate but identical webs O2 of cross directional elastic composite 1510. Each of the four webs O2 is then directed as web output O2 to a reel or spool. In further embodiments, the web output O2 of elastic composite 1510 may be packaged for easy handling and for further processing, or fed directly into a manufacturing process.

Elastic Composites Having Dead Zones

In further embodiments, the preferred elastic composite is equipped with a pair of non-elasticized regions or dead zones, the utility of which has already been described. As generally known, the dead zones are preferably situated on either lateral side of a central elastic region having an elastic construction (as discussed previously). Various ways are envisaged to create the dead zones within methods of making the elastic composite according to the invention. In one exemplary method, an adhesive pattern is applied to the nonwoven web input. The adhesive pattern is selectively applied so that adhesive is provided only to areas of the nonwoven web wherein the elastic strands are to be retained.

Figure 18:
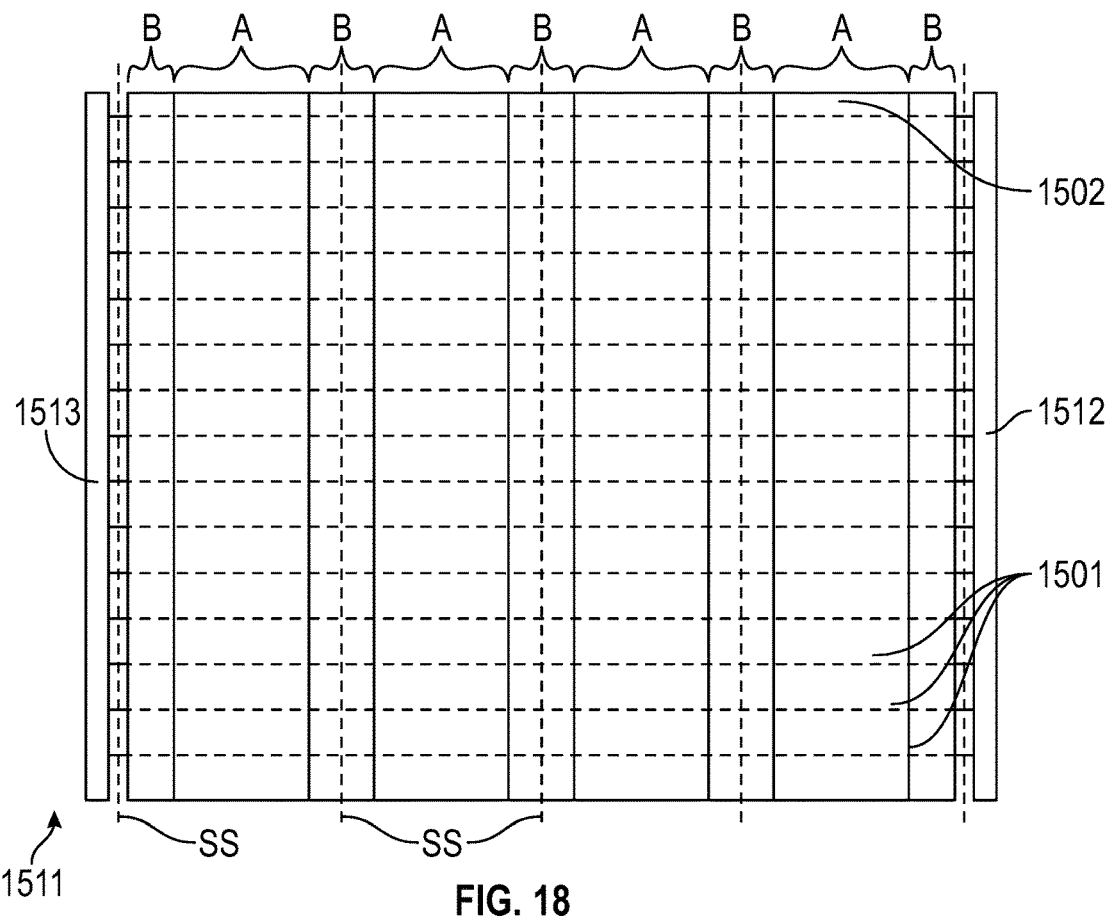
FIG. 18 is a simplified illustration of yet another elastic composite according to an embodiment of the present invention, in the form of an elastic laminate.

To illustrate, FIG. 18 shows an elastic composite laminate 1511 generated by a process such as that described above in respect to FIG. 16 and in a stage prior to passage of the web of the laminate 1511 through a set of slitting mechanisms. Tensioned elastic elements 1501 are sandwiched between the upper and lower nonwoven webs 1502, 1503 and extend between the carriers 1512, 1513. In this example, adhesive is applied only to prescribed areas of nonwoven webs 1512, 1513 ("adhered areas"), which areas are indicated as shaded areas A in FIG. 18. The adhesive application means 1616 described previously are precisely positioned over the path of the webs 1512, 1513 that correspond to the shaded areas A and operated to apply adhesive only to these areas A. The areas between the shaded areas A (i.e., "non-adhered areas" indicated as un-shaded areas B in FIG. 18) in the resulting laminate 1511 are clear of adhesive such that the portions of the elastic elements 1501 found therein remain loose. As indicated by slitting lines SS, slitting mechanisms provided downstream are aligned with the center of these non-adhered areas B. As the web of the laminate passes the slitters, the elastics in the non-adhered areas B are cut. Furthermore, the non-adhered areas B are divided into two sections. Each half section provides, thereafter, one non-elastic or dead zone of the multi-layered elastic composite 1510.

In the illustrated embodiment, a non-adhered area B is located adjacent each of the two carriers 1512, 1513 and a slitting line SS is aligned along the inside of the carrier 1512, 1513. As a result, the carrier 1512, 1513 is cut and removed from the web during the slitting process. The formerly adjacent non-adhered area B remains as a dead zone of the resulting cross-directional elastic composite.

Figure 19:
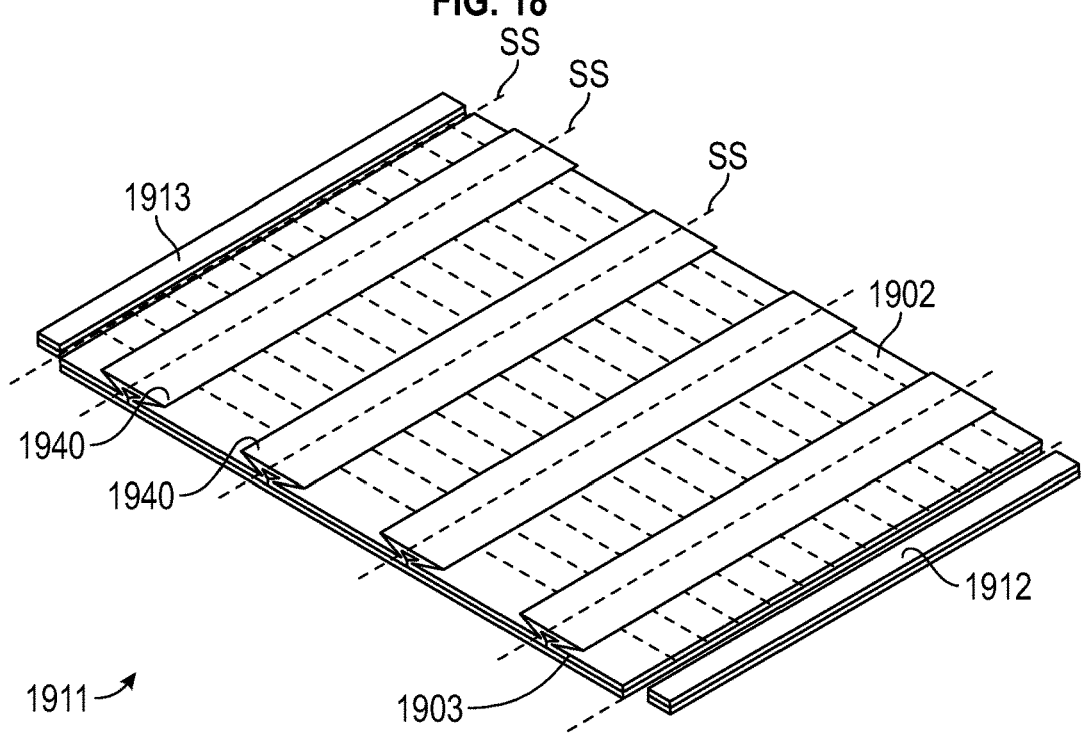
FIG. 19 is a simplified illustration of yet another elastic composite according to an embodiment of the present invention, in the form of an elastic laminate having pre-folded sections.

FIG. 19 illustrates yet another laminate 1911 (an elastic composite) in accordance with an embodiment of the invention. The illustrated laminate 1911 helps explain an alternate method of making a cross directional elastic composite featuring a pair of dead zones and a central elastic region therebetween. According to this method, the step of applying an upper (or lower) nonwoven web 1902 is modified by providing several folds 1940 in the nonwoven web 1902. A suitable folding sub-process is one substantially equivalent to the sub-process described in respect to FIGS. 6-10, and are now known in the art. The web 1902 is pre-folded to provide an excess folded section 1940 in the tensioned elastic composite O1' and in the resulting laminate 1911, as shown in FIG. 19 for the use of multiple folding boards. According to this embodiment, a slitting line SS is aligned with the center of each folded section 1940 much in the same manner as described above in respect to FIG. 18. In the slitting step, each folded section is divided into two separate folded sections and the elastic elements beneath the fold are severed. For each resulting individual elastic composite, the two folded sections are then unfolded to reveal dead zones on each side of a central elastic region.

Alternative Systems and System Components

FIG. 20 provides several simplified views of an alternative extender subsystem or, simply extender 2002 for receiving the continuous output (continuous web of elastic composite 1310) O1 and for further altering the configuration of the elastic composite 1310. The extender 2002 is employed to stretch the elastic composite 1310 and extend the lateral width XX of the web O1. Such extension may be executed just before or simultaneous with the application of other materials on the web O1. The extender 2002 also conveys the web of elastic composite O1 forwardly while maintain the elastics in tension.

Figure 21:
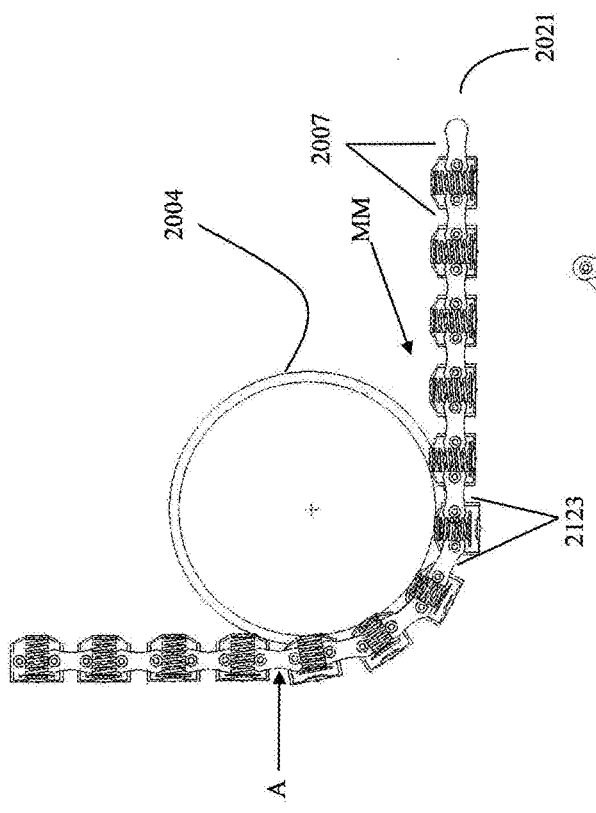
FIG. 21 is a detailed side view of an engagement mechanism, for use with the system of FIG. 20.

The extender 2002 employs a suitable conveying means in the form of a pair of endless belts or mechanical chains 2021, as shown in FIG. 21, and guides or rollers 2004. Referring to the side view of FIG. 20A, the chain 2021 is caused to move along a cyclical path through point A through point F. Affixed to the chain 2021 are engagement means 2007 that releasably attach the carriers 1312, 1313 with the moving chain 2021, thereby moving the web O1 forwardly. Referring to FIGS. 20A and 20B, the carriers 1312, 1313 are engaged at or about Point A in the cyclical path. The two chains 2021 are then caused to move forwardly, but along two divergent directions towards point B, thereby moving the carriers 1312, 1313 also along the divergent path. This stretches the individual elastics of the elastic composite 1310 and extends the lateral space XX to a target width. Between points B and C, the chains 2021 move in generally parallel relation. Other materials may be bonded to the elastic composite at this stage of the process (e.g., a nonwoven laminate).

At point C, the carriers 1312, 1313 are released by the engagement means 2007 and then conveyed to a subsequent, post-processing operation. The two endless chains 2021 are passed along generally convergent directions through points D to F before returning to point A.

Figure 22:
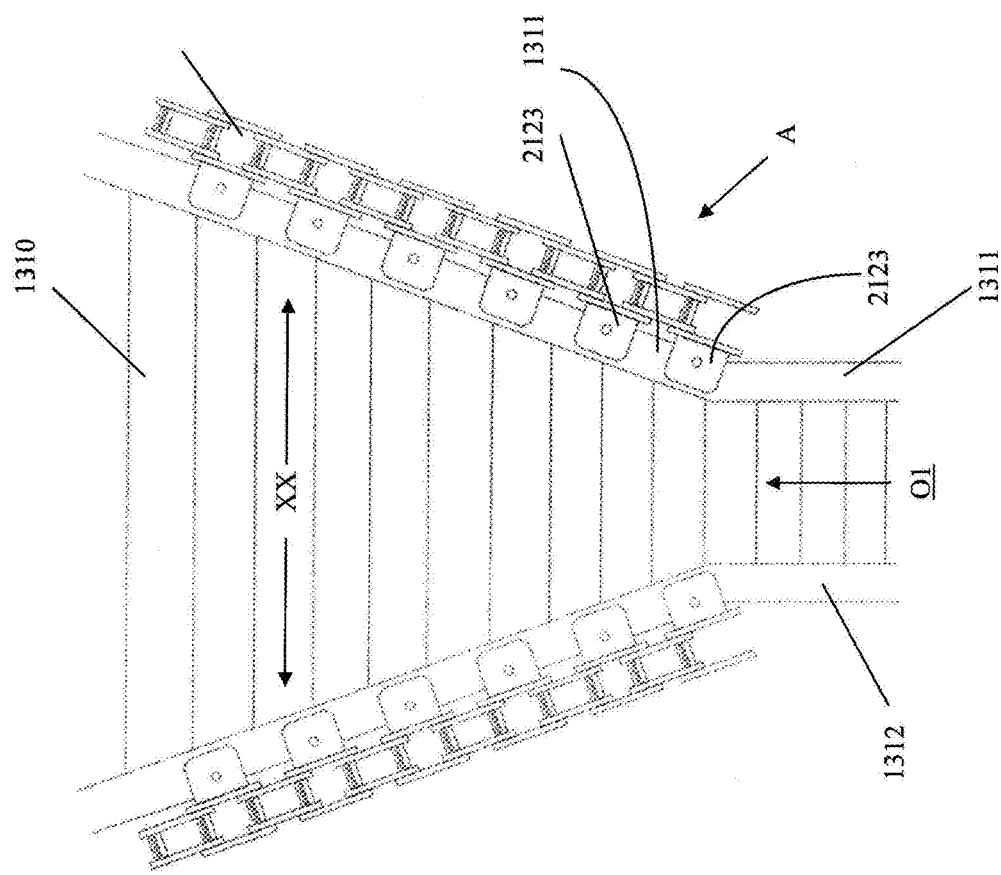
FIG. 22 is a plan view of the extender system employing the engagement mechanism of FIG. 21.

FIGS. 21 and 22 depict a suitable conveying means and an engagement means that attaches the carriers 1311, 1312 to the chain 2021. The chain 2021 is equipped (or includes) a series of gripper devices 2007 that includes movable clasps 2123. Suitable gripper devices and gripper chains are commercially available from Tsubakimoto Chain Co. of Japan. The gripper devices 2007 initiates the spring loaded, openable clasp 2123 to grip onto the topsides of the nonwoven carrier 1312, 1313. The clasp 2123 is opened when a force is exerted on the base of the gripper chain 2021 as in point MM in FIG. 21. This may be achieved by running the gripper chain 2021 about a roller 2004, such that the roller 2004 strikes the base of the clasps 2123, thereby opening or diverting the clasp 2123 from the chain 2012 ("opened"). Referring also to FIG. 20, the gripper chain 2012 is configured to open the clasp 2123 at about point A, which point the carrier 1311, 1312 engages the gripper chain 2021. The gripper chain 2021 is further configured to open the clasp 2123 at later point C in the path so that the web output O1 (preferably laminate) is released from the gripper chain 2021.

Other carrier engagement and gripper systems that may be used include a friction belt system, wherein the carrier is sandwiched between two belts and driven by the moving belts. In yet other embodiments, the engagement means may grip the carrier by way of a vacuum that secures the moving carrier to the periphery of each of a pair or set of reciprocating drums or wheels. In one example, the outside of the drums or wheels may be provided with perforations that fluidly communicate with an internal volume or medium that is at vacuum pressure.

Figure 24A:
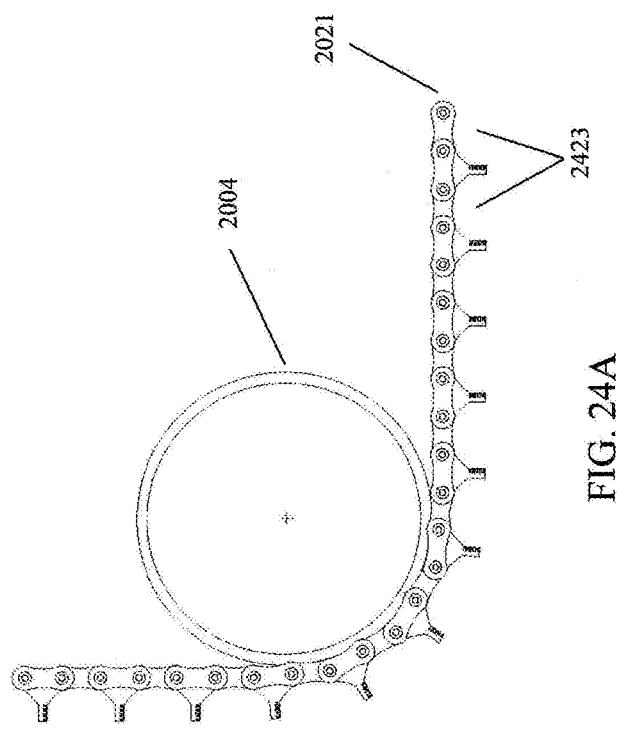
FIG. 24A is a detailed side view of yet another alternative engagement mechanism for use with the extender subsystem of FIG. 21.
Figure 23:
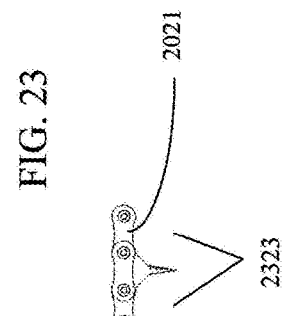
FIG. 23 is a detailed side view of an alternative engagement mechanism for use with the system of FIG. 21.
Figure 24B:
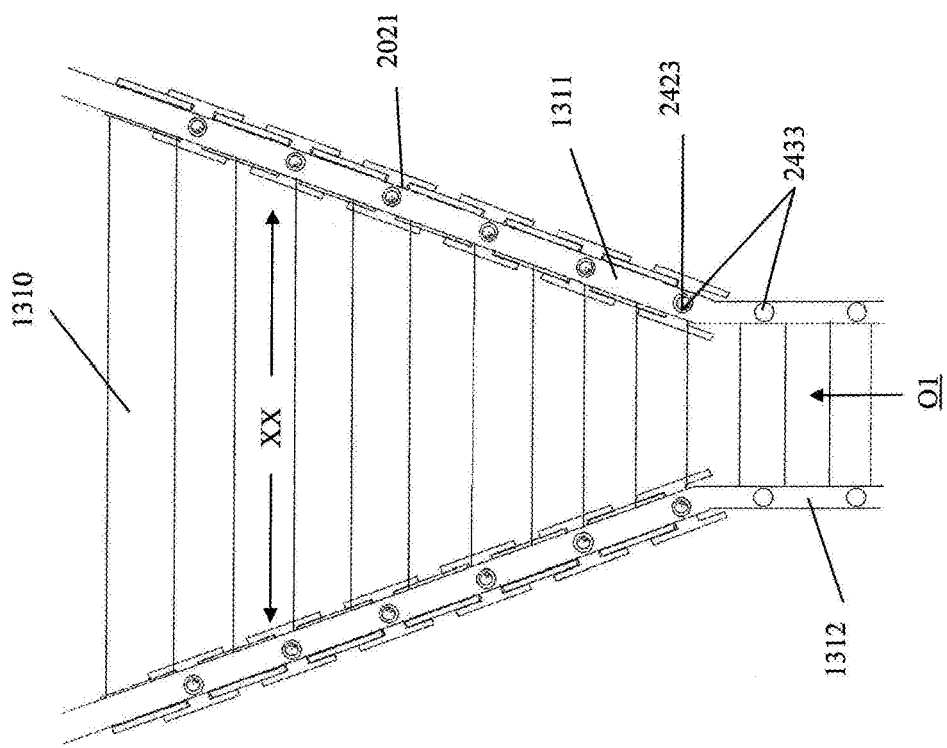
FIG. 24B is a plan view of the extender subsystem employing the engagement mechanism of FIG. 24A.
Figure 25:
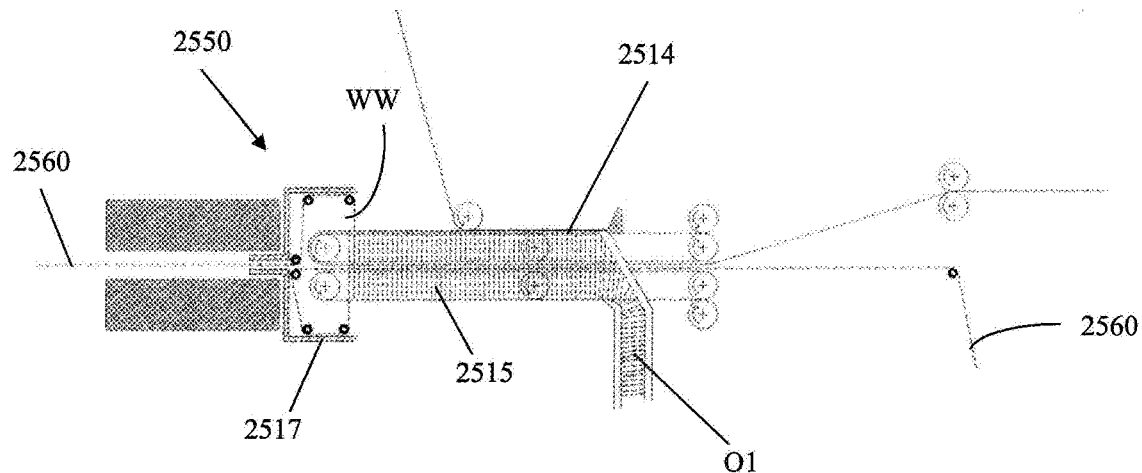
FIG. 25 is a simplified illustration of an alternative system of making an elastic composite, according to the present invention.

FIGS. 23 to 25 depict specific alternative means for engaging the carrier 1310, 1313 to the reciprocating chain 2021. In further alternative systems, the carrier may be presented to the extender with holes that allow pins or other protruding engagement means to engage the carrier. The non-woven for the carrier may be pre-supplied with the holes prior to entry into the inventive system. Alternatively, the carrier may be pierced by a piercing mechanism provided upstream of the extender. In FIG. 23, the engagement means employ a continuous row of needles or pins 2323 that are affixed to the chain 2021. The nonwoven carrier 1311, 1312 is punctured by the pins 2323 as it is received by the extender 2002 and is then conveyed by the moving chain 2021. FIGS. 24A and 24B depict yet another suitable conveying means and engagement means that includes a series of cylindrical extrusions 2423 affixed to the chain 2021. The cylindrical extrusions 2423 are configured to align and engage holes or recesses 2433 provided in the carrier 1311, as best shown in FIG. 24B. For each of the above alternative extender systems, the chain-type conveying means may be replaced with a belt.

Figure 13D:
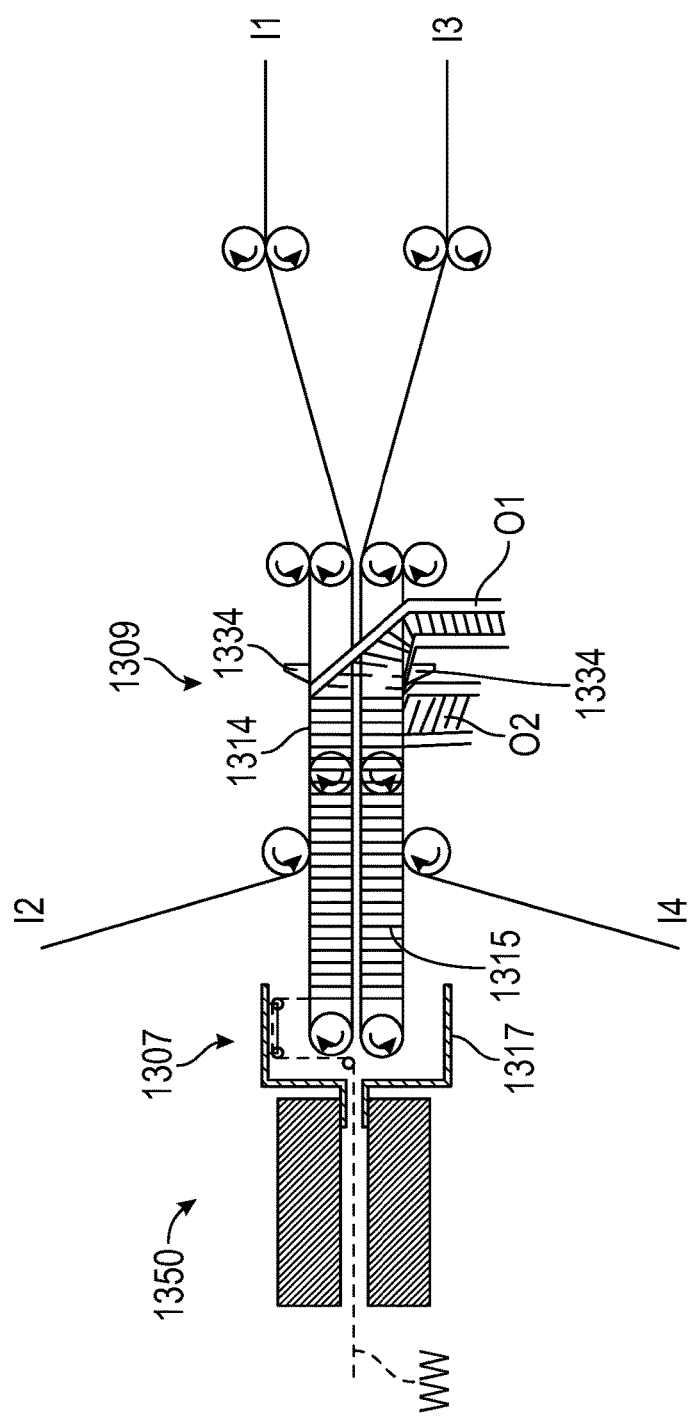
FIG. 13D is a simplified illustration of an alternative system of making elastic composites according to the invention.

FIG. 13D depicts an alternative system that employs or receives into the conveyor assembly 1309 two additional input webs of non-woven (I3 and I4) to double the output of the inventive system and process as described previously in respect to FIGS. 13A-C. As before, non-woven web input I1 is initially directed in between the upper and lower conveyors 1314, 1315, before being redirected and conveyed atop the upper conveyor 1314 whereon it receives the spun elastic WW. Then, the second nonwoven input I2 is applied over the transversely applied elastics WW and nonwoven input I1. In this embodiment, nonwoven input web I3 is also directed in between the upper and lower conveyors, in a manner similar to the conveyance of I2. The non-woven input I3 is, however, redirected and conveyed upon the lower conveyor 1315. With the nonwoven input I3 moving in the reverse direction on the lower conveyor 1315, the spin head 1317 applies elastic WW onto and about both conveyors 1414, 1315 and both I1, I3 during each revolution. With the elastics applied generally transversely thereupon, the fourth feed of nonwoven I4 is applied to the sub-composite of the non-woven I3 and elastic elements. Two multi-layer elastic composites or sandwiches are conveyed by the upper and lower conveyors 1314, 1315, respectively, while joined together by the continuous elastic strand WW. At this point, a slitter or other cutting mechanism 1334 placed in the path of each of the two composites preferably slits the composite centrally, thereby producing two separate but substantially identical carriers (as shown in FIG. 13D). With the slitters 1334 cutting the nonwoven webs centrally on the upper and bottom conveyors, the two resulting webs of elastic composite outputs O1, O2 conveniently slides to either side of the conveyor assembly 1309 and is received for further processing.

The pattern or application of elastics on the output web O1, and ultimately, on the resultant elastic composite 1310 may be altered in yet another way, as provided by the system shown in FIG. 25. The system 2550 of FIG. 25 is similar to that described in U.S. Patent Application Publication US-2008-0093015-A1, hereby incorporated as part of the present disclosure and for all purposes. In addition to a first source of elastic 2560, a second source of elastic 2561 ("dual feed") is provided to the system 2550 or more specifically, to the spin head 2507 for application about the conveyors 2514, 2515 and the webs of nonwoven input I1, I2. In preferred systems, the second feed 2561 is directed centrally from one side of the system 2550 opposite of the first feed 2560, as shown in FIG. 25 (and as described in US Pat. App. Publication US-2008-0093015-A1). With such a system modification, the pitch of the elastics applied may be increased. Furthermore, the speed of the process may be increased by increasing the speed of the conveyors (but without increasing the speed of the spin head).

Figure 26:
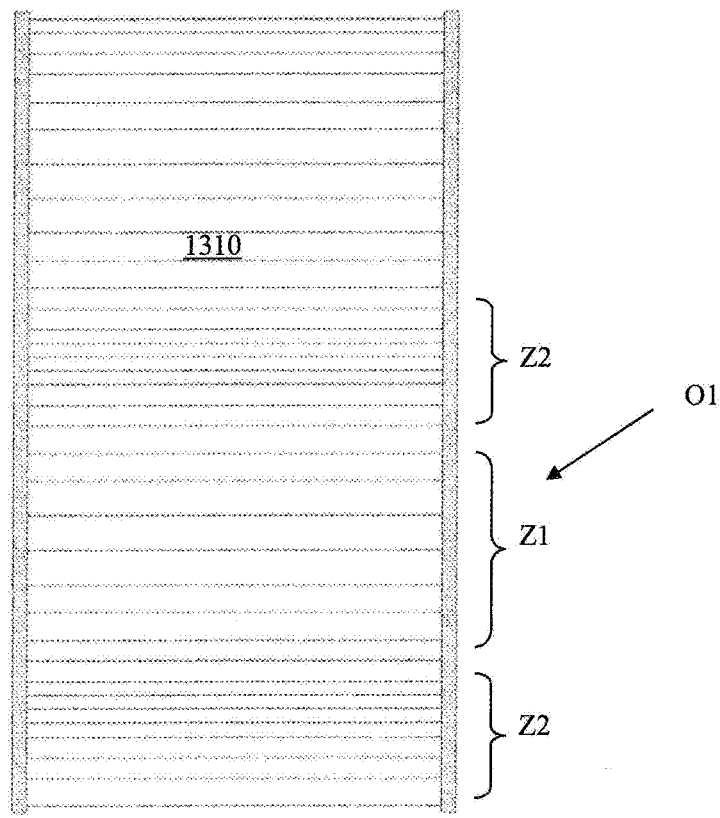
FIG. 26 is a simplified illustration of an output web of elastic composite, according to an alternative embodiment of the invention.

In further embodiments, the pitch of the elastics in the elastic composite may be varied to achieve desired functionality. FIG. 26 illustrates such an output web O1' of elastic composite having elastics elements 1310 arranged at different pitches. In this embodiment, a resultant web O1' has intermittent regions or zones of Z1 of normal pitch and normal elasticity followed by zones or regions Z2 of higher pitch and higher elasticity. The resultant output web O1 may be cut in a subsequent sub-process, at desired intervals, to provide sections of elastic composite having distinct elastic regions. The elastic composite sections will have areas of increased elasticity and areas of reduced elasticity. Such variance in pitch is preferably achieved by varying the speed of the conveyors, or, in alternative embodiments, by varying the speed of the spin head.

It is further noted that, with this embodiment, the speed of the process may be increased (doubled) relative to the "single feed" process, while maintaining the same number of elastic strands per unit length of the composite and without increasing the speed of the spinhead (but, by increasing the speed of the conveyor). Alternatively, the number of elastic strands per unit length may be increased (doubled) relative to the "single feed" process with the spinhead speed and conveyor speed unchanged.

In one particular application, the sections are cut such that the region proximate one cutting edge is generally provided with elastics at a higher pitch and thus, higher elasticity, while the region proximate the opposite edge is generally provided with elastics at reduced pitch and thus, at reduced elasticity. Such an elastic composite may be suited for application and use as waistband or side panel, wherein the region of higher elasticity is positioned along a top waist edge of the disposable absorbent article. In another embodiment, such an elastic composite and placement provide a combination waistband and side panel (see e.g., FIG. 27A-C and accompanying description). In yet further embodiments, the pitch of the elastic composites may be gradually varied as opposed to being abruptly changed. The resultant output web will, therefore, gather more gradually to give a smoother appearance, and provide a more continuous sealing barrier above the core and crotch regions of the disposable absorbent article.

FIGS. 27A, 27B, and 27C illustrate an advantageous application of the elastic composite 1310 according to the invention. Each of the Figures depict a disposable absorbent article 2710 having a central body 2711 with a first waist region 2712, a second waist region 2713, and a crotch or core region 2714 therebetween. The waist regions 2712, 2713 (and central body 2711) are further defined by a waist end edge 2720 and appropriately shaped side margins 2721.

In these applications, the elastic composite 1310 is implemented to impart elasticity to both the waistband and side panels of the disposable absorbent article 2710. In FIG. 27A, a laminated elastic composite 1310 is shown affixed across the waist end edge 2720 of the central body 2711, and more specifically, atop a topsheet 2718 of the disposable absorbent article 2710. The elastic composite 1310 provides a laminate or band that includes a first non-woven layer and a second non-woven layer sandwiching an arrangement of cross-directional elastics. The ends 2770 of the elastic band extend past side margins 2721 of the central body 2711. These ends 2770 provide the waist fastening ear regions or side panels of the disposable absorbent article 2710. The elasticized portion between these waist fastening ends 2770 is directly affixed to the end edge 2770 of the central body 2711 and imparts elasticity thereto. This portion provides the elastic waistband of the absorbent article 2710. In this way, the elastic composite band provides an efficient combination elastic waistband and pair of side panels of the disposable absorbent article. It should also be noted that in further embodiments, the elastic composite may be implemented in both the first and second waist regions 2712, 2713 of the article 2710.

In a typical manufacturing process, the elastic composite band is secured over the topsheet of the central body using suitable adhesive means and the like. As compared to conventional constructions, the combination waistband—side panels of the invention achieves a reduction in attachment steps and attachment points. In conventional constructions, each of the two side panels and the waistband is a separate multi-ply composite attached to a portion of the central body. Accordingly, the simpler construction of the combination waistband—side panel of the invention also provides materials cost savings. Furthermore, use of the elastic composite as a waistband replaces the need for and use of much more expensive elastic film or frame.

In a further embodiment illustrated by FIGS. 27B and 27C, an elastic composite 1310 of the invention combines with the materials of a standard disposable absorbent article 2710 to provide a more integral combination elasticized waist band and pair of side panels. In this embodiment, the elastic composite 1310 has an open elastic region 1304 and two nonwoven layered carriers 1311 at opposite ends. This elastic composite 1310 is simply applied over the backsheet 2719 (or to the "underside" of the topsheet 2718), whereby the open elastic region 1304 is situated between the side margins 2721 of the central body 2711 and along and inwardly of the waist end edge 2720. The topsheet 2718 is subsequently laid over the elastic composite 1310 to sandwich the open elastic region 1304 between the nonwoven layers. The elastic composite 1310 provides therefore, the elastic waistband of the disposable absorbent article 1310. Further in this embodiment, the carriers 1311 remain connected with the open elastic region 1304. After assembly, the carriers 1311 extend beyond the side margins 2721 of the central body 2711, thereby establishing the ear region or waist fastening side panels. Moreover, because the carriers 1311 remain connected with the elastic region, the side panels are laterally elasticized by the "waistband."

In an alternative design, both the topsheet and the backsheet of the central body of the disposable absorbent article are pre-shaped or pre-cut to provide regions that outline the side panel. The elastic composite of the invention is simply attached onto the backsheet (or topsheet), and then the topsheet (or backsheet) is laid over the elastic composite. Suitable adhesive means is used to secure the multi-layered composite. The carriers of the elastic composite, if still present, may be trimmed off to refine the shape and look of the side panel. Accordingly, a combination waistband and side panels is formed more integrally with the central body of the disposable absorbent article.

The use of the inventive elastic composite to form a combined waist and side panel provides certain important advantages over systems utilizing separate elastic materials as the side panel and waist elastic. Firstly, the elastic elements that form the elasticizing function of the waist panel and the side panels are the same, and as such, there is a continual connection of elastic material from one side panel to the opposite side panel as discussed above. As a result, any lateral force applied to the side panels is carried through and directly exerted around the waist of the wearer. This achieves added comfort for the wearer, and helps maintain the article in the correct position about the wearer. Moreover, the improve fit of the article about the wearer along with the reduction of attachments and adhered areas, improves the water-tight seal between the body of the wearer and the article.

The inventive combination waist panel and side panel also provides significant cost savings. The nonwoven carriers may be utilized as the side panel upon which a fastening element can be affixed. The elastic strands held between the nonwoven side edges provide the elastic material to elasticize the waist and side panels. The elastic composite allows for a practical and efficient way to process and place cross-machine direction strands in the waistband and side panel regions of the article. Using elastic strands in this way is far more cost efficient than using a stretchable film, foam or nonwoven for the waistband and/or side panels. Among other reasons, conventional films or foams are significantly more costly than elastic strands.

The foregoing description of the present invention has been presented for purposes of illustration and description. It is to be noted that the description is not intended to limit the invention to the various systems, apparatus, and processes disclosed herein. Various aspects of the invention, as described above, may be applicable to other types of disposable absorbent articles, garments, and the like, and processes for making the same. For example, the elastic composite described above, may be incorporated in other disposable absorbent garments such as training pants, etc. or in other areas or as other components of the garment. The elastic composite may also be incorporated into or with other garments, textiles, fabrics, and the like, or combinations thereof. The elastic composite may also incorporate different components. For example, the common use of nonwoven webs for the top and/or bottom sheet material may be replaced with use of another material such as a film material. Moreover, the various aspects of the process described in respect to FIGS. 11-27 may be utilized to produce compositions, garments and articles other than those described herein. Such variations of the invention will become apparent to one skilled in the relevant consumer products art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. A method of processing an elastic composite for incorporation into a disposable absorbent garment, said method comprising:
    providing said elastic composite comprising:
        a first nonwoven layered carrier;
        a second nonwoven layered carrier spaced from the first carrier; and
        a plurality of mutually spaced apart, cross-directional elastic elements extending generally laterally from the first carrier to the second carrier thereby forming an exposed elastic region therebetween, each carrier including at least a first nonwoven material layer, whereby said plurality of spaced apart elastic elements extend from the first carrier to the second carrier, and wherein the elastic elements have a first end and a second end, each end being secured by one of the layered carriers; and
    conveying the elastic composite forwardly in a machine direction by engaging the first and second carriers and moving the first and second carriers forwardly in the machine direction; and
    applying the elastic composite onto a central body of the disposable absorbent garment, thereby elasticizing a portion of the disposable absorbent garment; and
    wherein providing the elastic composite includes:
    conveying a first sheet of material;
    wrapping a section of elastic about the first sheet, thereby applying elastics cross directionally across the first sheet;
    applying a second sheet of material onto the first sheet having elastics applied thereon, thereby forming a subcomposite including the first sheet, the second sheet, and elastics sandwiched therebetween, wherein the elastics extend outward from one side of the subcomposite and encircle to return on an opposite side of the subcomposite; and
    cutting the sub-composite through the first and second sheets and the elastics to generate the elastic composite having two separated parts of the sub-composite and the exposed elastic region therebetween; and
    wherein said cutting includes separating the sub-composite into said first carrier and said second carrier, each carrier including a first material layer and a second material layer, whereby a plurality of spaced apart elastic elements extend from the first carrier to the second carrier, the first and second carriers defining the exposed elastic region therebetween.

2. The method of claim 1, wherein said conveying the elastic composite includes directing the first and second layered carriers in divergent forwardly directions, thereby extending a lateral width of the elastic region.

3. The method of claim 1, further comprising applying a material sheet over the elastic region during said conveying the elastic composite, thereby generating an elasticized central region having at least one material layer.

4. The method of claim 1, wherein said conveying a first sheet conveys the first sheet of material on a conveyor and said wrapping wraps the section of elastic about the first sheet and the conveyor.

5. The method of claim 1, further comprising:
    applying a sheet of material onto one side of the elastic region and applying a second sheet of material onto a second side of the elastic region, thereby creating a multilayered laminate having the two material layers and cross directional elasticity; and
    slitting the laminate along one or more slitting lines to separate therefrom, a plurality of multi-layer elastic composites.

6. The method of claim 5, wherein the material layers are non-woven material layers, and wherein at least one of said applying a first sheet and applying a second sheet includes applying adhesive to multiple designated areas of one or more of the sheets of material such that the resulting laminate includes adhered areas of the elastic region corresponding to the designated areas wherein the two nonwoven material layers mutually adhere to sandwich a plurality of elastics therebetween and non-adhered areas wherein the nonwoven layers are not mutually adhered; and
    wherein said slitting includes slitting the laminate along the non-adhered areas to divide the non-adhered area and sever the elastics within the non-adhered area, such that each of the plurality of said multi-layer elastic composites includes a central elastic region corresponding to an adhered area and non-elastic zone adjacent the central elastic that corresponds to portion of a non-adhered area among said non-adhered areas.

7. The method of claim 5, wherein said applying a second sheet includes prefolding at least two sections of the sheet of material prior to contact with the elastic region, such that the resulting laminate includes at least two folded flaps above the plurality of elastics; and
    wherein said slitting includes slitting the laminate along the folded flap to sever the elastics beneath the folded flap, said method further comprising:
    unfolding the folded flaps of each of the resulting cross-directional elastic composites to reveal a non-elastic zone therein, the non-elastic zone being positioned adjacent a multi-layered elastic region.

8. The method of claim 5, further comprising cutting said laminate along the machine direction proximate each carrier to sever said carriers from said laminate.

9. The method of claim 1, wherein said applying said elastic composite onto said central body includes,
    forming a disposable absorbent article having a topsheet, backsheet, an absorbent core therebetween, and a central body defined, at least partly, by the topsheet and backsheet, the central body having opposing waist regions along each of two waist end edges that are longitudinally spaced apart and define the longitudinal length of the central body; and wherein said forming the disposable absorbent article includes affixing said elastic composite along one waist end edge of said central body, thereby elasticating a waistband portion.

10. The method of claim 9, wherein said affixing includes extending said elastic composite such that said carriers extend past side margins of the central body, thereby providing waist fastening regions.

11. The method of claim 1, further comprising:

providing a backsheet of the disposable absorbent article; and applying a topsheet to said backsheet, thereby forming a central body of the disposable absorbent article having said central body and a pair longitudinally spaced part waist regions each including a waist end edge of the central body; and wherein said applying said elastic composite includes applying said elastic composite on said backsheet prior to said applying said topsheet, wherein said elastic composite is situated between said topsheet and backsheet along a waist end region.

12. A method of processing an elastic composite for incorporation into a disposable absorbent garment, said method comprising:

providing said elastic composite comprising:
- a first nonwoven layered carrier;
- a second nonwoven layered carrier spaced from the first carrier; and
- a plurality of mutually spaced apart, cross-directional elastic elements extending generally laterally from the first carrier to the second carrier thereby forming an exposed elastic region therebetween, each carrier including at least a first nonwoven material layer, whereby said plurality of spaced apart elastic elements extend from the first carrier to the second carrier, and wherein the elastic elements have a first end and a second end, each end being secured by one of the layered carriers; and conveying the elastic composite forwardly in a machine direction by engaging the first and second carriers and moving the first and second carriers forwardly in the machine direction; and applying the elastic composite onto a central body of the disposable absorbent garment, thereby elasticizing a portion of the disposable absorbent garment; and wherein said conveying the elastic composite includes directing the first and second layered carriers in divergent forwardly directions, thereby extending a lateral width of the elastic region.

13. A method of processing an elastic composite for incorporation into a disposable absorbent garment, said method comprising:

providing said elastic composite comprising:
- a first nonwoven layered carrier;
- a second nonwoven layered carrier spaced from the first carrier; and
- a plurality of mutually spaced apart, cross-directional elastic elements extending generally laterally from the first carrier to the second carrier thereby forming an exposed elastic region therebetween, each carrier including at least a first nonwoven material layer, whereby said plurality of spaced apart elastic elements extend from the first carrier to the second carrier, and wherein the elastic elements have a first end and a second end, each end being secured by one of the layered carriers; and conveying the elastic composite forwardly in a machine direction by engaging the first and second carriers and moving the first and second carriers forwardly in the machine direction; and applying the elastic composite onto a central body of the disposable absorbent garment, thereby elasticizing a portion of the disposable absorbent garment; and applying a sheet of material onto one side of the elastic region and applying a second sheet of material onto a second side of the elastic region, thereby creating a multilayered laminate having the two material layers and cross directional elasticity; and slitting the laminate along one or more slitting lines to separate therefrom, a plurality of multi-layer elastic composites.

14. The method of claim 13, wherein said conveying the elastic composite includes directing the first and second layered carriers in divergent forwardly directions, thereby extending a lateral width of the elastic region.

15. The method of claim 13, wherein providing the elastic composite includes:

conveying a first sheet of material;

wrapping a section of elastic about the first sheet, thereby applying elastics cross directionally across the first sheet;

applying a second sheet of material onto the first sheet having elastics applied thereon, thereby forming a subcomposite including the first sheet, the second sheet, and elastics sandwiched therebetween, wherein the elastics extend outward from one side of the subcomposite and encircle to return on an opposite side of the subcomposite; and cutting the sub-composite through the first and second sheets and the elastics to generate the elastic composite having two separated parts of the sub-composite and the exposed elastic region therebetween; and wherein said cutting includes separating the sub-composite into said first carrier and said second carrier, each carrier including a first material layer and a second material layer, whereby a plurality of spaced apart elastic elements extend from the first carrier to the second carrier, the first and second carriers defining the exposed elastic region therebetween.

16. The method of claim 13, wherein the material layers are non-woven material layers, and wherein at least one of said applying a first sheet and applying a second sheet includes applying adhesive to multiple designated areas of one or more of the sheets of material such that the resulting laminate includes adhered areas of the elastic region corresponding to the designated areas wherein the two nonwoven material layers mutually adhere to sandwich a plurality of elastics therebetween and non-adhered areas wherein the nonwoven layers are not mutually adhered; and wherein said slitting includes slitting the laminate along the non-adhered areas to divide the non-adhered area and sever the elastics within the non-adhered area, such that each of the plurality of said multi-layer elastic composites includes a central elastic region corresponding to an adhered area and non-elastic zone adjacent the central elastic that corresponds to portion of a non-adhered area among said non-adhered areas.

17. The method of claim 13, wherein said applying a second sheet includes prefolding at least two sections of the sheet of material prior to contact with the elastic region, such that the resulting laminate includes at least two folded flaps above the plurality of elastics; and
wherein said slitting includes slitting the laminate along the folded flap to sever the elastics beneath the folded flap, said method further comprising:
unfolding the folded flaps of each of the resulting cross-directional elastic composites to reveal a non-elastic zone therein, the non-elastic zone being positioned adjacent a multi-layered elastic region.

18. The method of claim 13, further comprising cutting said laminate along the machine direction proximate each carrier to sever said carriers from said laminate.

* * * * *